US012570977B2

(12) United States Patent
Lin et al.

(10) Patent No.: US 12,570,977 B2
(45) Date of Patent: Mar. 10, 2026

(54) mRNA COMPOSITION AND PRODUCTION METHOD FOR USE IN ANTI-VIRAL AND ANTI-CANCER VACCINES

(71) Applicants: Shi-Lung Lin, Arcadia, CA (US); Samantha Chang-Lin, Arcadia, CA (US); Jack SK Chen, Taipei (TW); David TS Wu, Taipei (TW); Chia-Ning Shen, Taipei (TW); Mei-Jung Wang, Taipei (TW)

(72) Inventors: Shi-Lung Lin, Arcadia, CA (US); Samantha Chang-Lin, Arcadia, CA (US); Jack SK Chen, Taipei (TW); David TS Wu, Taipei (TW); Chia-Ning Shen, Taipei (TW); Mei-Jung Wang, Taipei (TW)

(73) Assignees: MELLO BIOTECH TAIWAN CO., LTD., Taipei City (TW); ACADEMIA SINICA, Taipei City (TW)

( * ) Notice: Subject to any disclaimer, the term of this patent is extended or adjusted under 35 U.S.C. 154(b) by 182 days.

(21) Appl. No.: 17/489,357

(22) Filed: Sep. 29, 2021

(65) Prior Publication Data
US 2022/0396798 A1 Dec. 15, 2022

Related U.S. Application Data

(60) Provisional application No. 63/222,666, filed on Jul. 16, 2021, provisional application No. 63/209,969, filed on Jun. 12, 2021, provisional application No. 63/210,988, filed on Jun. 15, 2021, provisional application No. 63/213,258, filed on Jun. 22, 2021.

(51) Int. Cl.
| | |
|---|---|
| *C12N 15/11* | (2006.01) |
| *C12N 15/113* | (2010.01) |
| *C12N 15/85* | (2006.01) |

(52) U.S. Cl.
CPC ...... *C12N 15/1135* (2013.01); *C12N 15/1131* (2013.01); *C12N 15/85* (2013.01); *C12N 2310/141* (2013.01); *C12N 2310/531* (2013.01); *C12N 2840/203* (2013.01)

(58) Field of Classification Search
CPC .................... C12N 2310/531; C12N 2840/203
See application file for complete search history.

(56) References Cited

U.S. PATENT DOCUMENTS

| | | | | |
|---|---|---|---|---|
| 2005/0255089 A1* | 11/2005 | Chiorini | ................. | C12N 15/86 435/235.1 |
| 2006/0073500 A1* | 4/2006 | Peters | ..................... | C12P 19/34 435/5 |
| 2006/0078551 A1* | 4/2006 | Gopalakrishnakone | ..................... | C12Q 1/34 424/94.2 |
| 2019/0010485 A1* | 1/2019 | Yazdan Panah | ....... | C12N 15/10 |

FOREIGN PATENT DOCUMENTS

| | | | | |
|---|---|---|---|---|
| WO | WO-2017162265 A1 * | 9/2017 | .............. | A61P 31/16 |
| WO | WO-2019232103 A1 * | 12/2019 | ......... | A61K 31/7105 |

OTHER PUBLICATIONS

Le Tinevez et al , Selective inhibition of cell-free translation by oligonucleotides targeted to a mRNA hairpin structure, Nucleic Acid Research, 1998, vol. 26, No. 10: 2273-2278 (Year: 1998).*

Borman et al , Comparison of picornaviral IRES-driven internal initiation of translation in cultured cells of different origins, Nucleic Acid Research, 1997, vol. 25, No. 5: 925-932 (Year: 1997).*

Bochkov et al , Translational efficiency of EMCV IRES in bicistronic vectors is dependent upon IRES sequence and gene location, BioTechniques, 2006, 41: 283-292 (Year: 2006).*

Ko et al, Development of an RNA Expression Platform Controlled by Viral Internal Ribosome Entry SitesJ. Microbiol. Biotechnol., 2019, 29(1), 127-140 with Supplemental materials pp. 1-18 (Year: 2019).*

Rao et al , siRNA vs. shRNA: Similarities and differences, Advanced Drug Delivery Reviews, 2009, 61: 746-759 (Year: 2009).*

Chen et al , Structural Basis for Helicase-Polymerase Coupling in the SARS-CoV-2 Replication-Transcription Complex, Cell, Sep. 17, 2020, 182: 1560-1573 (Year: 2020).*

Hillen et al , Structure of replicating SARS-CoV-2 polymerase, Nature, published online May 21, 2020, 584: 154-159 (Year: 2020).*

* cited by examiner

*Primary Examiner* — Ekaterina Poliakova-Georgantas
(74) *Attorney, Agent, or Firm* — Birch, Stewart, Kolasch & Birch, LLP

(57) ABSTRACT

This invention relates to a novel mRNA composition and its production method useful for developing and manufacturing RNA-based anti-viral and/or anti-cancer vaccines and medicines. This invention includes two types of mRNA constructs, namely "5'-hairpin messenger RNA (5hmRNA)" and "messenger-hairpin-messenger RNA (mhmRNA)", respectively. Both of 5hmRNA and mhmRNA contain at least a hairpin-like stem-loop RNA structure. The 5hmRNA contains at least a stem-loop RNA structure in the 5'-UTR of a protein/peptide-coding mRNA, while the mhmRNA contains a middle stem-loop structure flanked with two protein/peptide-coding mRNA sequences on both sides. In mhmRNA, the first 5'-mRNA preferably encodes an RNA replicase, for amplifying the second 3'-mRNA in transfected cells. After transfection into target cells, 5hmRNA and mhmRNA can be further translated into at least a desired protein/peptide. To produce highly structured 5hmRNA and mhmRNA, a novel PCR-IVT methodology has been developed and used with a specially designed RNA polymerase-helicase mixture reaction.

15 Claims, 9 Drawing Sheets
Specification includes a Sequence Listing.

1x    2x

← PCR product

← mhmRNA
  (12.5k)

mRNA COMPOSITION AND PRODUCTION METHOD FOR USE IN ANTI-VIRAL AND ANTI-CANCER VACCINES

PRIORITY

The present invention claims priority to U.S. Provisional Patent Application No. 63/209,969 filed on Jun. 12, 2021, which is entitled "Novel mRNA Composition and Production for Use in Anti-Viral and Anti-Cancer Vaccines". The present invention also claims priority to U.S. Provisional Patent Applications No. 63/210,988 filed on Jun. 15, 2021, No. 63/213,258 filed on Jun. 22, 2021, and No. 63/222,666 filed on Jul. 16, 2021, all of which are entitled "Novel mRNA Composition and Production Method for Use in Anti-Viral and Anti-Cancer Vaccines".

REFERENCE TO SEQUENCE LISTING SUBMITTED VIA EFS-WEB

This application includes an electronically submitted sequence listing in .txt format. The .txt file contains a sequence listing entitled "5199-0336PUS2_ST25.txt" created on Nov. 1, 2021 and is 5,607 bytes in size. The sequence listing contained in this .txt file is part of the specification and is hereby incorporated by reference herein in its entirety.

FIELD OF INVENTION

This invention generally relates to a novel mRNA composition and its production method useful for developing and manufacturing RNA-based anti-viral and/or anti-cancer vaccines and medicines. The mRNA so obtained can be used for producing not only preventive but also therapeutic vaccines and/or medicines. The present invention includes two types of related mRNA constructs, namely "5'-hairpin messenger RNA (5hmRNA)" and "messenger-hairpin-messenger RNA (mhmRNA)", respectively. In brief, both of 5hmRNA and mhmRNA contain at least a hairpin-like stem-loop structure (i.e. perfectly or imperfectly matched either single or multiple hairpin RNA). The 5hmRNA contains at least a stem-loop RNA structure in the 5'-untranslated region (5'-UTR) of a protein/peptide-coding mRNA, while the mhmRNA contains a middle stem-loop RNA structure flanked with two protein/peptide-coding mRNA sequences on both sides. In mhmRNA, the first 5'-mRNA preferably encodes RNA replicase, such as viral RNA-dependent RNA polymerase (RdRp), for amplifying the second 3'-mRNA in transfected cells. After transfected into target cells, both of 5hmRNA and mhmRNA can be further translated into at least a desired protein/peptide for eliciting a pre-designed, desired biological effect or cellular function, including but not limited to inducing specific immune responses, preventing viral infections, suppressing viral replication, inhibiting viral assembly, and/or inhibiting tumor/cancer cell growth as well as causing cancer cell death. To produce highly structured 5hmRNA and mhmRNA, a novel PCR-IVT methodology has been developed and used with a specially designed RNA polymerase-helicase mixture reaction.

BACKGROUND

Polymerase chain reaction-in vitro transcription (PCR-IVT) methods have been widely used for sense messenger RNA (mRNA) and antisense RNA (aRNA) production for over twenty years (FIG. 1). However, the IVT reaction is still not useful for producing hairpin-like RNAs because hairpin-like stem-loop structures are signals of intrinsic transcription termination for prokaryotic RNA polymerases (McDowell et al, *Science* 266:822-825, 1994). As a result, prior PCR-IVT methods using prokaryote-associated RNA polymerases cannot overcome the low efficiency problem of hairpin-like RNA production.

The combinational use of PCR-IVT methods to produce mRNAs and/or RNA-DNA hybrids was first reported by Lin et al (U.S. Pat. Nos. 7,662,791, 8,080,652, 8,372,969, and 8,609,831 to Lin). As shown in FIG. 1, Lin's methods first use PCR and/or reverse transcription (RT) to incorporate a specific RNA promoter-primer into the resulting PCR products in order to generate promoter-driven DNA templates for IVT. Next, an IVT reaction is performed to produce and amplify desired RNA molecules from the DNA templates (Lin et al, *Methods Mol Biol.* 221:93-101, 2003). Then, an optional RT reaction may be done for generating RNA-DNA hybrids, of which the DNA part protects the desired RNAs (i.e. mRNAs) from degradation. Under DNA protection, the RNA-DNA hybrids can be subjected to further mRNA modifications, such as adding 5'-cap and/or 3'-poly(A) tail to the desired RNAs/mRNAs (Lin S L, *Methods Mol Biol.* 221:289-293, 2003). After that, the DNA part is removed using RNase-free DNase digestion and the modified RNAs/mRNAs can be formulated with a delivery agent and then transfected into target cells for producing desired proteins/peptides. Alternatively, the desired RNAs may be transfected into cells to generate piwi-interacting RNAs (piRNA) for silencing specific target genes (U.S. Pat. Nos. 8,372,969 and 8,609,831 to Lin). Yet, although Lin's methods have been successfully used to produce mRNAs and piRNAs for eliciting at least a specific biological and cellular effect, these mRNAs and piRNAs are not hairpin-like or hairpin-containing RNAs. As a result, Lin's prior PCR-IVT methods did not disclose an effective way to overcome the low efficiency problem of hairpin-like RNA generation in vitro.

Traditional mRNA production methods are largely based on a part or whole of Lin's PCR-IVT concept and methodology (U.S. Pat. Nos. 7,662,791, 8,080,652, 8,372,969, and 8,609,831 to Lin). Clearly, it is easy for an ordinary skillful person in the art to anticipate the use of Lin's methodology for producing a part or whole of mRNA and/or mRNA-cDNA hybrid sequences in vitro. Notably, some commercial semi- or fully-automated IVT devices had been designed and developed using Lin's concept and methodology. Yet, these prior mRNA production methods and devices still did not provide any effective solution to overcome the problem of hairpin-like RNA production. To solve this problem, another kind of methods using plasmid-driven RNA expression in prokaryotes (i.e. bacteria) had been developed by Lin et al (U.S. Pat. Nos. 9,637,747 and 9,783,811 to Lin). These prokaryote-produced mRNAs may contain multiple hairpin-like stem-loop structures. In this approach, a chemical transcription inducer is added into medium of prokaryotic cell culture to overcome the problem of intrinsic transcription termination caused by hairpin RNAs (McDowell et al, *Science* 266:822-825, 1994), resulting in a marked increase of hairpin-like RNA production. Nevertheless, this plasmid-driven RNA expression method requires prokaryotic cells and is limited in prokaryotes.

It is not reasonable for an ordinary skillful person in the art to anticipate the in-vitro generation of hairpin-like or hairpin-containing mRNA for vaccine/medicine production because it is widely known that a hairpin-like RNA structure not only hinders mRNA transcription but also may interfere with certain mRNA processing, such as 5'-capping and modification. In traditional concept, the presence of a hair-pin-like structure in mRNA may even hinder protein trans-lation from the mRNA. Thus, the low efficiency problem of highly structured RNA production greatly hinders the devel-opment of mRNA vaccines and medicines.

Generation and use of 5'-end or middle hairpin-/stem-loop-containing mRNA constructs for designing and devel-oping vaccines/medicines is one of key novelties of the present invention. To this, none of prior PCR-IVT methods can overcome the low efficiency problem of hairpin-like RNA production. Therefore, an improved PCR-IVT method for increasing the efficiency of highly structured RNA generation remains highly desirable.

SUMMARY OF THE INVENTION

The principle of the present invention is relied on the production of "5'-hairpin messenger RNA (5hmRNA)" and/or "messenger-hairpin-messenger RNA (mhmRNA)" (FIG. 2), using a novel enzymatic PCR-IVT system, and the use of 5hmRNA or mhmRNA, or both, for designing and devel-oping pharmaceutical and therapeutic applications, such as vaccines and/or medicines, both of which are useful for anti-viral and/or anti-cancer therapy. To achieve this goal, a highly efficient PCR-IVT method is crucial because both 5hmRNA and mhmRNA are highly structured mRNAs and prior PCR-IVT methods are not effective for producing highly structured RNAs. Clearly, it is conceivable that a novel method of highly structured RNA production is required for not only efficient 5hmRNA/mhmRNA manu-facture but also its cost reduction, leading to the develop-ment of more affordable and effective mRNA vaccines/medicines for the public use.

Traditionally, it is not reasonable for an ordinary skillful person in the art to anticipate the in-vitro generation of hairpin-like or hairpin-containing mRNA for vaccine/medi-cine production because it is widely known that the presence of a hairpin RNA structure in 5'-UTR not only hinders mRNA transcription but also inhibits protein translation from the mRNA. To solve this problem, the present inven-tion adopts a novel IVT reaction system with a mixture of RNA polymerase and helicase activities. The addition of helicase activity in IVT markedly reduces the secondary structures of both DNA templates and the resulting mRNA products for far more efficiently producing highly structured mRNAs. Accordingly, an improved buffer system is also required to maintain and enhance the efficiency of mixed RNA polymerase and helicase activities in IVT. Interest-ingly, several prior studies had reported that helicase may be involved in prokaryotic transcription termination; yet, the present invention shows a totally different function of heli-case in mRNA production during IVT. Alternatively, we have recently found that certain viral replicases, such as coronaviral RNA-dependent RNA polymerases (RdRp) with an additional helicase activity, may be used for producing highly structured mRNAs as well.

Several prior studies have proposed the use of natural internal ribosome entry sites (IRES) for mRNA vaccine development (Schlake et al, *RNA biology* 9:1319-1330, 2012; Ko et al, *J. Micobiol. Biotechnol.* 29:127-140, 2019). However, because these natural IRES are highly structured RNA motifs, the resulting low production rate severely hinders its development. To overcome this problem, the present invention herein provides a novel PCR-IVT method with a new RNA polymerase-helicase mixture activity, which is useful for not only markedly increasing highly structured mRNA production but also reducing the production costs thereof. As a result, the low production rate problem of prior IRES-containing mRNA vaccine develop-ment can be now solved by using the present invention.

In the structures of 5hmRNA and mhmRNA produced by the present invention, a special design of 5'-hairpin-like stem-loop RNA structure not only can stimulate intracelluar RNA processing enzymes to remove hairpin(s) and then add 5'-cap in all following mRNA sequences but also may simultaneously generate at least a small hairpin RNA (shRNA), similar to siRNA and microRNA precursor (pre-miRNA), which can further function to silence at least a specific target gene, such as cellular, viral and/or cancer-associated genes. It has also been noted that RNA processing enzymes may not be able to process all kinds of 5'-hairpin-like stem-loop RNA structures, but just certain specially designed ones. After further investigation, our studies sug-gest that some specially designed stem-loop RNA structures may also function as an artificial internal ribosome entry site (IRES) for initiating and enhancing the translation of a following mRNA with or without a cap structure. As a result, under both of processed and unprocessed conditions, these specially designed stem-loop RNA structures can facilitate protein/peptide synthesis from the following mRNA.

In one preferred embodiment (FIG. 2), 5hmRNA mainly consists of two parts: 5'-stem-loop RNA and 3'-mRNA. In principle, the 5'-stem-loop RNA contains at least a perfectly or imperfectly matched either single or multiple hairpin structure, preferably ranging about 10~800 nucleotides in length, and a short spacer sequence located between the stem-loop structure and the start codon of the following 3'-mRNA, preferably ranging about 1500 nucleotides apart in length. When there are multiple hairpin structures in the 5'-stem-loop RNA, a spacer sequence must be placed between every two hairpin RNA structures, preferably rang-ing about 2~500 nucleotides apart in length. For example as listed in SEQ.ID.NO.3~SEQ.ID.NO.15, the hairpin struc-tures and spacers may possess either same or different sequences, respectively. Also, the 5'-stem-loop RNA may function as an artificial IRES mimic for initiating and enhancing the translation of the 3'-mRNA. On the other hand, the 3'-mRNA not only encodes at least one desired protein or peptide but also contains either a 5'-AAUAAA-3' (SEQ.ID.NO.1) or a 5'-AAUUAAA-3' (SEQ.ID.NO.2) sequence in its 3'-end. After mRNA translation, the resulting proteins/peptides can lead to at least a biological function or effect of interest, including but not limited to inducing specific immune responses, preventing viral infections, sup-pressing viral assembly, inhibiting viral replication, and/or inhibiting tumor/cancer cell growth as well as causing cancer cell death.

In another preferred embodiment (FIG. 2), mhmRNA is formed by adding an additional mRNA (5'-mRNA) sequence in the 5'-end of 5hmRNA. As a result, the stem-loop RNA now functions as a middle separator to set apart the individual translation of the first 5'-mRNA and the next 3'-mRNA into either same or different proteins/peptides, respectively. Moreover, similar to 5hmRNA, the stem-loop RNA structure not only stimulates intracellular RNA pro-cessing enzymes to remove hairpin(s) and add 5'-cap in the 3'-mRNA but also may further generate at least a shRNA and/or piRNA for silencing at least a specific target gene of interest. These target genes may include a variety of disease-associated cellular and/or pathogenic genes, such as cellular, viral and/or cancer-associated genes. Alternatively, an arti-ficial IRES-like 5'-stem-loop RNA structure may be placed in the 5'-UTR of either 5'-mRNA or 3'-mRNA, or both, for initiating and enhancing the translation of the 5'-mRNA and/or 3'-mRNA, respectively, leading to multiple desired protein/peptide production.

In third preferred embodiment, the first 5'-mRNA of mhmRNA encodes an RNA replicase, such as viral RNA-dependent RNA polymerase (RdRp), for use in amplifying the next 3'-mRNA in transfected cells. This kind of RNA replicase/RdRp-expressing mhmRNA is self-amplifiable in the transfected cells, hence also called self-amplifiable mRNA (samRNA). After transfection into target cells, both of 5hmRNA and mhmRNA can be further processed and translated into at least a desired protein/peptide for eliciting a pre-designed, desired biological effect or function, including but not limited to inducing specific immune responses, preventing viral infections, suppressing viral replication/assembly and/or inhibiting tumor/cancer cell growth as well as causing cancer cell death. Also, the resulting mRNAs may be served as a template for RdRp to generate piRNAs, leading to at least a specific gene silencing effect, as described in our prior U.S. Pat. Nos. 8,372,969 and 8,609,831 (to Lin). For example, when the resulting mRNA encodes a targeted viral gene, the piRNAs so obtained will be useful for developing vaccines to silence the viral gene activity and thus preventing viral infection.

The stem-loop RNA structures of 5hmRNA and mhmRNA may further contain at least one of the following single or multiple hairpin-like sequences as listed:

(1)
```
                                    (SEQ.ID.NO. 3)
5'-GCUCCCUUCA ACUUUAACAU GGAAGUGCUU UCUGUGACUU

UAAAAGUAAG UGCUUCCAUG UUUUAGUAGG AGU-3' (73-nt)
```

(2)
```
                                    (SEQ.ID.NO. 4)
5'-CCUUUGCUUU AACAUGGGGG UACCUGCUGU GUGAAACAAA

AGUAAGUGCU UCCAUGUUUC AGUGGAGG-3' (68-nt)
```

(3)
```
                                    (SEQ.ID.NO. 5)
5'-CCACCACUUA AACGUGGAUG UACUUGCUUU GAAACUAAAG

AAGUAAGUGC UUCCAUGUU UUGGUGAUGG-3' (69-nt)
```

(4)
```
                                    (SEQ.ID.NO. 6)
5'-CCUCUACUUU AACAUGGAGG CACUUGCUGU GACAUGACAA

AAAUAAGUGC UUCCAUGUUU GAGUGUGG-3' (68-nt)
```

(5)
```
                                    (SEQ.ID.NO. 7)
5'-CUGUGUGGCU GUCACUCGGC UGCAUGCUUA GUGCACUCAC

GCAG-3' (44-nt)
```

(6)
```
                                    (SEQ.ID.NO. 8)
5'-CUGUGUGGCU GUCACUCGGC UGCAUGCUUA GUGCACUCAC

GCAGUAUAAU UAAUAACUAA UUACU-3' (65-nt)
```

(7)
```
                                    (SEQ.ID.NO. 9)
5'-GUCGUUGACA GGACACGAGU AACUCGUCUA UCUUCUGCAG

GCUGCUUACG GUUUCGUCCG UGUUGCAGCC GAUCAUCAGC

ACAUCUAGGU UUCGUCCGGG UGUGACCGAA AGGUAAGAUG

GAGAGCCUUG UCCCUGGUUU CAACGAG-3' (147-nt)
```

-continued (8)
```
                                    (SEQ.ID.NO. 10)
5'-AAUUAUAAAU UACCAGAUGA UUUUACAGGC UGCGUUAUAG

CUUGGAAUUC UAACAAUCUU GAUUCUAAGG UUGGUGGUAA

UUAUAAUU-3' (88-nt)
```

(9)
```
                                    (SEQ.ID.NO. 11)
5'-CACAAAUAUU ACCAGAUCCA UCAAAACCAA GCAAGAGGUC

AUUUAUUGAA GAUCUACUUU UCAACAAAGU GACACUUGCA

GAUGCUGGCU UCAUCAAACA AUAUGGUGAU UGCCUUGGUG

AUAUUGCUG-3' (129-nt)
```

(10)
```
                                    (SEQ.ID.NO. 12)
5'-GCAAAAUGU GAUCUUGCUU GUAAAUACAA UUUUGAGAGG

UUAAUAAAUU ACAAGUAGUG CUAUUUUUGU AUUUAGGUUA

GCUAUUUAGC UUUACGUUCC AGGAUGCCUA GUGGCAGCCC

CACAAUAUCC AGGAAGCCCU CUCUGCGGUU UUUCAGAUUC

GUUAGUCGAA AAACCUAAGA AAUUUAAUG-3' (189-nt)
```

(11)
```
                                    (SEQ.ID.NO. 13)
5'-CACUCCCCUG UGAGGACUAC UGUCUUCACG CAGAAAGCGU

CUAGCCAUGG CGUUAGUAUG AGUGUCGUGC AGCCUCCAGG

ACCCCCCCUC CCGGGAGAGC CAUAGUGGUC UGCGGAACCG

GUGAGUACAC CGGAAUUGCC AGGACGACCG GGUCCUUUCU

UGGAUCAACC CGCUCAAUGC CUGGAGAUUU GGGCGUGCCC

CCGCGAGACU GCUAGCCGAG UAGUGUUGGG UCGCGAAAGG

CCUUGUGGUA CUGCCUGAUG GGUGCUUGCG AGUGCCCCGG

GAGGUCUCGU AGAC-3' (294-nt)
```

(12)
```
                                    (SEQ.ID.NO. 14)
5'-GGACACGAGU AACUCGUCUA UCUUCUGCAG GCUGCUUACG

GUUUCGUCCG UGUUG-3' (55-nt)
```

(13)
```
                                    (SEQ.ID.NO. 15)
5'-CAGCCGAUCA UCAGCACAUC UAGGUUUUGU CCGGGUGUGA

CCGAAAGGUA AG-3' (52-nt)
```

For facilitating the delivery of either 5hmRNA or mhmRNA, or both, into desired target cells in vitro, ex vivo and/or in vivo, the 5hmRNA and mhmRNA can be mixed, conjugated, encapsulated and/or formulated with at least a delivery agent selected from glycylglycerins, liposomes, nanoparticles, liposomal nanoparticles, conjugating molecules, infusion chemicals, gene gun materials, electroporation particles, transposons, and a combination thereof.

The advantages of using 5hmRNA and/or mhmRNA as vaccine or medicine include (1) no need to add any 5'-cap in vitro and so as to save costs and reduce contamination, (2) resulting in more stable mRNA products which are well protected by the stem-loop RNA structures, (3) forming 100% capped mRNAs in transfected cells after intracellular RNA processing enzymes remove the stem-loop structures, (4) may further possessing artificial IRES-like motif/mimic for initiating and enhancing protein/peptide synthesis from the mRNA, (5) forming self-amplifiable mRNAs with an encoded replicase/RdRp activity, (6) resulting in high yield of protein/peptide production derived from self-amplifiable mhmRNAs, and (7) co-expressing at least a shRNA and/or piRNA useful for silencing at least a specific target gene of interest, such as viral and/or cancer-associated genes. The 5hmRNA and/or mhmRNA may contain at least a modified nucleotide for enhancing its stability. As a result, it is conceivable that these novel 5hmRNA and mhmRNA compositions are useful for designing and developing new pharmaceutical and therapeutic applications, such as vaccines and medicines, for use in anti-viral and/or anti-cancer therapy.

A. Definitions

To facilitate understanding of the invention, a number of terms are defined below:

Nucleic Acid: a polymer of deoxyribonucleic acid (DNA) or ribonucleic acid (RNA), either single or double stranded.

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. A nucleoside containing at least one phosphate group bonded to the 3' or 5' position of the pentose is a nucleotide. DNA and RNA are consisted of different types of nucleotide units called deoxyribonucleotide and ribonucleotide, respectively.

Oligonucleotide: a molecule comprised of two or more monomeric units of DNA and/or RNA, preferably more than three, and usually more than ten. An oligonucleotide longer than 13 nucleotide monomers is also called polynucleotide. The exact size will depend on many factors, which in turn depends on the ultimate function or use of the oligonucleotide. The oligonucleotide may be generated in any manner, including chemical synthesis, DNA replication, RNA transcription, reverse transcription, or a combination thereof.

Nucleotide Analog: a purine or pyrimidine nucleotide that differs structurally from adenine (A), thymine (T), guanine (G), cytosine (C), or uracil (U), but is sufficiently similar to substitute for the normal nucleotide in a nucleic acid molecule.

Nucleic Acid Composition: a nucleic acid composition refers to an oligonucleotide or polynucleotide such as a DNA or RNA sequence, or a mixed DNA/RNA sequence, in either a single-stranded or a double-stranded molecular structure.

Gene: a nucleic acid composition whose oligonucleotide or polynucleotide sequence codes for an RNA and/or a polypeptide (protein). A gene can be either RNA or DNA. A gene may encode a non-coding RNA, such as small hairpin RNA (shRNA), microRNA (miRNA), rRNA, tRNA, snoRNA, snRNA, and their RNA precursors as well as derivatives. Alternatively, a gene may encode a protein-coding RNA essential for protein/peptide synthesis, such as messenger RNA (mRNA) and its RNA precursors as well as derivatives. In some cases, a gene may encode a protein-coding RNA that also contains at least a microRNA or shRNA sequence.

Primary RNA Transcript: an RNA sequence that is directly transcribed from a gene without any RNA processing or modification.

Precursor messenger RNA (pre-mRNA): primary RNA transcripts of a protein-coding gene, which are produced by eukaryotic type-II RNA polymerase (Pol-II) machineries in eukaryotes through an intracellular mechanism termed transcription. A pre-mRNA sequence contains a 5'-untranslated region (UTR), a 3'-UTR, exons and introns.

Intron: a part or parts of a gene transcript sequence encoding non-protein-reading frames, such as in-frame intron, 5'-UTR and 3'-UTR.

Exon: a part or parts of a gene transcript sequence encoding protein-reading frames (cDNA), such as cDNA for cellular genes, growth factors, insulin, antibodies and their analogs/homologs as well as derivatives.

Messenger RNA (mRNA): assembly of pre-mRNA exons, which is formed after intron removal by intracellular RNA splicing machineries (e.g. spliceosomes) and served as a protein-coding RNA for peptide/protein synthesis. The peptides/proteins encoded by mRNAs include, but not limited, enzymes, growth factors, insulin, antibodies and their analogs/homologs as well as derivatives.

Complementary DNA (cDNA): a single-stranded or double-stranded DNA that contains a sequence complementary to an mRNA sequence and does not contain any intronic sequence.

Sense: a nucleic acid molecule in the same sequence order and composition as the homologous mRNA. The sense conformation is indicated with a "+", "s" or "sense" symbol.

Antisense: a nucleic acid molecule complementary to the respective mRNA molecule. The antisense conformation is indicated as a "−" symbol or with an "a" or "antisense" in front of the DNA or RNA, e.g., "aDNA" or "aRNA".

Base Pair (bp): a partnership of adenine (A) with thymine (T), or of cytosine (C) with guanine (G) in a double stranded DNA molecule. In RNA, uracil (U) is substituted for thymine. Generally the partnership is achieved through hydrogen bonding. For example, a sense nucleotide sequence "5'-A-T-C-G-U-3" can form complete base pairing with its antisense sequence "5'-A-C-G-A-T-3".

5'-end: a terminus lacking a nucleotide at the 5' position of successive nucleotides in which the 5'-hydroxyl group of one nucleotide is joined to the 3'-hydroyl group of the next nucleotide by a phosphodiester linkage. Other groups, such as one or more phosphates, may be present on the terminus.

3'-end: a terminus lacking a nucleotide at the 3' position of successive nucleotides in which the 5'-hydroxyl group of one nucleotide is joined to the 3'-hydroyl group of the next nucleotide by a phosphodiester linkage. Other groups, most often a hydroxyl group, may be present on the terminus.

Template: a nucleic acid molecule being copied by a nucleic acid polymerase. A template can be single-stranded, double-stranded or partially double-stranded, RNA or DNA, depending on the polymerase. The synthesized copy is complementary to the template, or to at least one strand of a double-stranded or partially double-stranded template. Both RNA and DNA are synthesized in the 5' to 3' direction. The two strands of a nucleic acid duplex are always aligned so that the 5' ends of the two strands are at opposite ends of the duplex (and, by necessity, so then are the 3' ends).

Nucleic Acid Template: a double-stranded DNA molecule, double-stranded RNA molecule, hybrid molecules such as DNA-RNA or RNA-DNA hybrid, or single-stranded DNA or RNA molecule.

Conserved: a nucleotide sequence is conserved with respect to a pre-selected (referenced) sequence if it non-randomly hybridizes to an exact complement of the pre-selected sequence.

Homologous or Homology: a term indicating the similarity between a polynucleotide and a gene or mRNA sequence. A nucleic acid sequence may be partially or completely homologous to a particular gene or mRNA sequence, for example. Homology may be expressed as a percentage determined by the number of similar nucleotides over the total number of nucleotides.

Complementary or Complementarity or Complementation: a term used in reference to matched base pairing between two polynucleotides (i.e. sequences of an mRNA and a cDNA) related by the aforementioned "base pair (bp)" rules. For example, the sequence "5'-A-G-T-3" is complementary to not only the sequence "5'-A-C-T-3" but also to "5'-A-C-U-3". Complementation can be between two DNA strands, a DNA and an RNA strand, or between two RNA strands. Complementarity may be "partial" or "complete" or "total". Partial complementarity or complementation occurs when only some of the nucleic acid bases are matched according to the base pairing rules. Complete or total complementarity or complementation occurs when the bases are completely or perfectly matched between the nucleic acid strands. The degree of complementarity between nucleic acid strands has significant effects on the efficiency and strength of hybridization between nucleic acid strands. This is of particular importance in amplification reactions, as well as in detection methods that depend on binding between nucleic acids. Percent complementarity or complementation refers to the number of mismatch bases over the total bases in one strand of the nucleic acid. Thus, a 50% complementation means that half of the bases were mismatched and half were matched. Two strands of nucleic acid can be complementary even though the two strands differ in the number of bases. In this situation, the complementation occurs between the portion of the longer strand corresponding to the bases on that strand that pair with the bases on the shorter strand.

Complementary Bases: nucleotides that normally pair up when DNA or RNA adopts a double stranded configuration.

Complementary Nucleotide Sequence: a sequence of nucleotides in a single-stranded molecule of DNA or RNA that is sufficiently complementary to that on another single strand to specifically hybridize between the two strands with consequent hydrogen bonding.

Hybridize and Hybridization: the formation of duplexes between nucleotide sequences which are sufficiently complementary to form complexes via base pairing. Where a primer (or splice template) "hybridizes" with target (template), such complexes (or hybrids) are sufficiently stable to serve the priming function required by a DNA polymerase to initiate DNA synthesis. There is a specific, i.e. non-random, interaction between two complementary polynucleotides that can be competitively inhibited.

Posttranscriptional Gene Silencing: a targeted gene knockout or knockdown effect at the level of mRNA degradation or translational suppression, which is usually triggered by either foreign/viral DNA or RNA transgenes or small inhibitory RNAs.

RNA Interference (RNAi): a posttranscriptional gene silencing mechanism in eukaryotes, which can be triggered by small inhibitory RNA molecules such as microRNA (miRNA), small hairpin RNA (shRNA) and small interfering RNA (siRNA). These small RNA molecules usually function as gene silencers, interfering with expression of intracellular genes containing either completely or partially complementarity to the small RNAs.

Gene Silencing Effect: a cell response after a gene function is suppressed, consisting but not limited of cell cycle attenuation, G0/G1-checkpoint arrest, tumor suppression, anti-tumorigenecity, cancer cell apoptosis, and a combination thereof.

Non-coding RNA: an RNA transcript that cannot be used to synthesize peptides or proteins through intracellular translation machineries. Non-coding RNA includes long and short regulatory RNA molecules such as microRNA (miRNA), small hairpin RNA (shRNA), small interfering RNA (siRNA) and double strand RNA (dsRNA). These regulatory RNA molecules usually function as gene silencers, interfering with expression of intracellular genes containing either completely or partially complementarity to the non-coding RNAs.

MicroRNA (miRNA): single-stranded RNAs capable of binding to targeted gene transcripts that have partial complementarity to the miRNA. MiRNA is usually about 17-27 oligonucleotides in length and is able to either directly degrade its intracellular mRNA target(s) or suppress the protein translation of its targeted mRNA, depending on the complementarity between the miRNA and its target mRNA. Natural miRNAs are found in almost all eukaryotes, functioning as a defense against viral infections and allowing regulation of gene expression during development of plants and animals.

Precursor MicroRNA (Pre-miRNA): hairpin-like single-stranded RNAs containing stem-arm and stem-loop regions for interacting with intracellular RNaseIII endoribonucleases to produce one or multiple microRNAs (miRNAs) capable of silencing a targeted gene or genes complementary to the microRNA sequence(s). The stem-arm of a pre-miRNA can form either a perfectly (100%) or a partially (mis-matched) hybrid duplexes, while the stem-loop connects one end of the stem-arm duplex to form a circle or hairpin-loop conformation. In the present invention, however, precursor of microRNA may also includes pri-miRNA.

Small interfering RNA (siRNA): short double-stranded RNAs sized about 18-27 perfectly base-paired ribonucleotide duplexes and capable of degrading target gene transcripts with almost perfect complementarity.

Small or short hairpin RNA (shRNA): single-stranded RNAs that contain a pair of partially or completely matched stem-arm nucleotide sequences divided by an unmatched loop or bubble oligonucleotide to form a hairpin-like structure. Many natural miRNAs are derived from small hairpin-like RNA precursors, namely precursor microRNA (pre-miRNA).

Vector: a recombinant nucleic acid composition such as recombinant DNA (rDNA) capable of movement and residence in different genetic environments. Generally, another nucleic acid is operatively linked therein. The vector can be capable of autonomous replication in a cell in which case the vector and the attached segment is replicated. One type of preferred vector is an episome, i.e., a nucleic acid molecule capable of extrachromosomal replication. Preferred vectors are those capable of autonomous replication and expression of nucleic acids. Vectors capable of directing the expression of genes encoding for one or more polypeptides and/or non-coding RNAs are referred to herein as "expression vectors" or "expression-competent vectors". Particularly important vectors allow cloning of cDNA from mRNAs produced using a reverse transcriptase. A vector may contain components consisting of a viral or a type-II RNA polymerase (Pol-II or pol-2) promoter, or both, a Kozak consensus translation initiation site, polyadenylation signals, a plurality of restriction/cloning sites, a pUC origin of replication, a SV40 early promoter for expressing at least an antibiotic resistance gene in replication-competent prokaryotic cells, an optional SV40 origin for replication in mammalian cells, and/or a tetracycline responsive element. The structure of a vector can be a linear or circular form of single- or double-stranded DNA selected form the group consisting of plasmid, viral vector, transposon, retrotransposon, DNA transgene, jumping gene, and a combination thereof.

Promoter: a nucleic acid to which a polymerase molecule recognizes, perhaps binds to, and initiates RNA transcription. For the purposes of the instant invention, a promoter can be a known polymerase binding site, an enhancer and the like, any sequence that can initiate synthesis of RNA transcripts by a desired polymerase.

Restriction Site: a DNA motif for restriction enzyme cleavage including but not limited AatII, AccI, AflIII/III, AgeI, ApaI/LI, AseI, Asp718I, BamHI, BbeI, BclI/II, BglII, BsmI, Bsp120I, BspHI/LU11I/120I, BsrI/BI/GI, BssHII/SI, BstBI/U1/XI, ClaI, Csp6I, DpnI, DraI/II, EagI, Ecl136II, EcoRI/RII/47III/RV, EheI, FspI, HaeIII, HhaI, HinPI, HindIII, HinfI, HpaI/II, KasI, KpnI, MaeII/III, MfeI, MluI, MscI, MseI, NaeI, NarI, NcoI, NdeI, NgoMI, NotI, NruI, NsiI, PmlI, Ppu10I, PstI, PvuI/II, RsaI, SacI/II, SalI, Sau3AI, SmaI, SnaBI, SphI, SspI, StuI, TaiI, TaqI, XbaI, XhoI, XmaI cleavage site.

Cistron: a sequence of nucleotides in a DNA molecule coding for an amino acid residue sequence and including upstream and downstream DNA expression control elements.

RNA Processing: a cellular mechanism responsible for RNA maturation, modification and degradation, including RNA splicing, intron excision, exosome digestion, nonsense-mediated decay (NMD), RNA editing, RNA processing, 5'-capping, 3'-poly(A) tailing, and a combination thereof.

Gene Delivery: a genetic engineering method selected from the group consisting of polysomal transfection, liposomal transfection, chemical (nanoparticle) transfection, electroporation, viral infection, DNA recombination, transposon insertion, jumping gene insertion, microinjection, gene-gun penetration, and a combination thereof.

Genetic Engineering: a DNA recombination method selected from the group consisting of DNA restriction and ligation, homologous recombination, transgene incorporation, transposon insertion, jumping gene integration, retroviral infection, and a combination thereof.

Tumor Suppression: a cellular anti-tumor and anti-cancer mechanism consisting but not limited of cell cycle attenuation, G0/G1-checkpoint arrest, tumor suppression, antitumorigenecity, cancer cell apoptosis, and a combination thereof.

Targeted Cell: a single or a plurality of human cells selected from the group consisting of a somatic cell, a tissue cell, a stem cell, a germ-line cell, a tumor cell, a cancer cell, a virus-infected cell, and a combination thereof.

Cancerous Tissue: a neoplastic tissue derived from the group consisting of skin cancer, prostate cancer, breast cancer, liver cancer, lung cancer, brain tumor/cancer, lymphoma, leukemia and a combination thereof.

Antibody: a peptide or protein molecule having a preselected conserved domain structure coding for a receptor capable of binding a pre-selected ligand.

Pharmaceutical and/or therapeutic Application: a biomedical utilization and/or apparatus useful for stem cell generation, stem cell research and/or therapy development, cancer therapy, disease treatment, wound healing and tissue regeneration treatment, high-yield production of drug and/or food supplies, and a combination thereof.

Prokaryote or Prokaryotic Cell: an one-cell organism that lacks a distinct membrane-bound nucleus and has its genetic materials in the form of a continuous strand of DNA, such as bacteria.

Eukaryote or Eukaryotic Cell: an one-cell or multiple-cell organism whose cells contain a nucleus and other structures (organelles) enclosed within membranes, such as yeast, plant and animal cells.

Transcription Inducer: a chemical agent that can induce and/or enhance eukaryotic RNA and/or gene transcription from a eukaryotic pol-2 or pol-2 equivalent promoter in prokaryotic cells. For example, a transcription inducer contains, but not limited, a chemical structure similar to 3-morpholinopropane-1-sulfonic acid (MOPS), ethanol and/or glycerin, as well as their functional analogs, such as mannitol, 2-(N-morpholino)ethanesulfonic acid (IVIES) and 4-(2-hydroxyethyl)-1-piperazineethanesulfonic acid (HEPES), or a mixture thereof.

B. Compositions and Applications

A novel mRNA composition and its production method for use in anti-viral and anti-cancer vaccine manufacture and development, comprising:

at least a 5'-hairpin messenger RNA (5hmRNA) and/or messenger-hairpin-messenger RNA (mhmRNA), or both, wherein the 5hmRNA contains at least a stem-loop RNA structure in the 5'-UTR region of a protein/peptide-coding mRNA and the mhmRNA contains at least a middle stem-loop RNA structure flanked with two same or different mRNA sequences on its both sides.

To overcome the low efficiency problem of hairpin-like RNA production, the 5hmRNA and mhmRNA are produced using a novel PCR-IVT methodology with a newly invented RNA polymerase-helicase mixture activity and an improved IVT buffer system. Also, for facilitating the delivery of either 5hmRNA or mhmRNA, or both, into target cells, the 5hmRNA and mhmRNA can be further mixed, conjugated, encapsulated and/or formulated with at least a delivery agent selected from glycylglycerins, liposomes, nanoparticles, liposomal nanoparticles, conjugating molecules, infusion chemicals, gene gun materials, transposons, electroporation particles, and a combination thereof.

In one preferred embodiment, 5hmRNA mainly consists of two parts: 5'-stem-loop RNA and 3'-mRNA (FIG. 2). Structurally, the 5'-stem-loop RNA contains at least a perfectly or imperfectly matched either single or multiple hairpin structure, preferably ranging about 10~800 nucleotides in length, and a short spacer sequence located between the stem-loop structure and the start codon of the following 3'-mRNA, preferably ranging about 1~500 nucleotides apart in length. When there are multiple hairpin-like structures in the 5'-stem-loop RNA, a spacer sequence must be placed between every two hairpin RNA structures, preferably ranging about 2~500 nucleotides apart in length. The hairpin structures and spacers may possess either same or different sequences, respectively. Also, the 5'-stem-loop RNA may further function as an artificial IRES-like mimic for initiating and enhancing the translation of the 3'-mRNA, leading to desired protein/peptide production. On the other hand, the 3'-mRNA not only encodes at least one desired protein or peptide but also contains either a 5'-AAUAAA-3' (SEQ.ID.NO.1) or a 5'-AAUUAAA-3' (SEQ.ID.NO.2) sequence near its 3'-end for inducing intracellular poly(A) tailing mechanisms.

In another preferred embodiment, mhmRNA is formed by adding an additional mRNA (5'-mRNA) sequence in the 5'-end of 5hmRNA. As a result, the stem-loop RNA now functions as a middle separator to set apart the individual translation of the first 5'-mRNA and the next 3'-mRNA into either same or different proteins/peptides, respectively. Moreover, similar to 5hmRNA, the stem-loop RNA structure not only stimulates intracellular RNA processing enzymes to add 5'-cap in the 3'-mRNA but also may further generate at least a shRNA and/or piRNA for silencing at least a target gene of interest. These specific target genes may include a variety of disease-associated cellular and/or pathogenic genes, such as viral and/or cancer-related genes. Alternatively, an additional IRES-like 5'-stem-loop RNA structure may be placed in the 5'-UTR of either 5'-mRNA or 3'-mRNA, or both, for initiating and enhancing the translation of the 5'-mRNA and/or 3'-mRNA, leading to multiple desired protein/peptide production.

In third preferred embodiment (FIG. 2), the first 5'-mRNA of mhmRNA encodes an RNA replicase, such as viral RNA-dependent RNA polymerase (RdRp), for amplifying the second 3'-mRNA in transfected cells. This kind of RNA replicase/RdRp-expressing mhmRNA is self-amplifiable in the transfected cells. After transfection into target cells, both of 5hmRNA and mhmRNA can be further processed and translated into at least a desired protein/peptide for eliciting a pre-designed, desired biological effect or function, including but not limited to inducing specific immune responses, preventing viral infections, suppressing viral replication/assembly, and/or inhibiting tumor/cancer cell growth as well as causing cancer cell death. As a result, it is conceivable that such novel 5hmRNA and mhmRNA compositions are very useful for designing and developing new pharmaceutical and/or therapeutic applications, such as vaccines and/or medicines, for use in anti-viral and/or anti-cancer therapy.

The stem-loop RNA structures of 5hmRNA and mhmRNA may contain at least a sequence selected from SEQ.ID.NO.3, SEQ.ID.NO.4, SEQ.ID.NO.5, SEQ.ID.NO.6, . . . to SEQ.ID.NO.15, and/or a combination thereof.

BRIEF DESCRIPTION OF THE DRAWINGS

Referring particularly to the drawings for the purpose of illustration only and not limitation, there is illustrated.

EXAMPLES

1. Human Cell Culture and In-Vitro RNA Transfection

Figure 6:
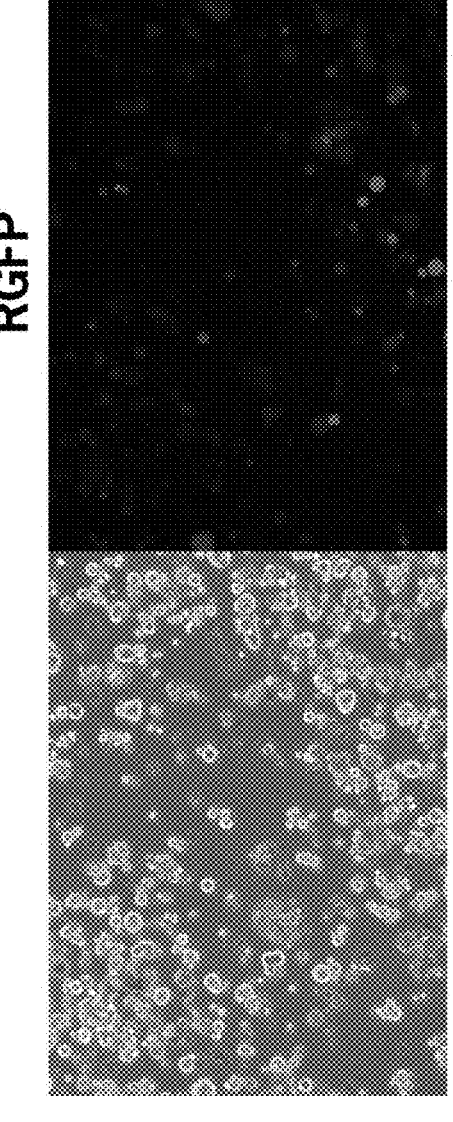
FIG. 6 shows the resulting RGFP protein (red fluorescent color) production in the A549 cells transfected by the invented PCR-IVT-made 5hmRNA (from FIG. 3), indicating that desired proteins/peptides can be successfully produced from the 5hmRNA in the transfected cells, so as to deliver a designed biological and/or cellular effect. It is conceivable that the encoded RGFP mRNA can be replaced by any other protein/peptide-coding mRNA sequence in the 5hmRNA and mhmRNA, so as to deliver a different biological effect or cellular function of interest.
Figure 9:
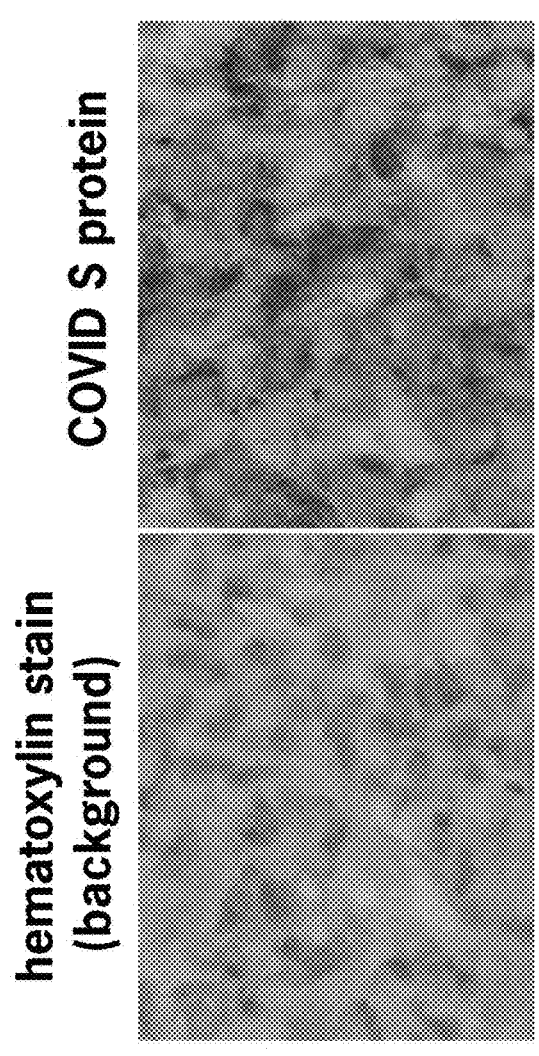
FIG. 9 shows the immunostaining results of coronaviral (e.g. COVID-19) S 2 proteins produced in the BEAS-2B cells after transfected with the anti-viral 5hmRNA (from FIG. 7), indicating that the delivery of anti-viral 5hmRNA into BEAS-2B lung epithelial cell line can induce intracellular production of coronaviral S 2 protein, which is useful for trigger antiviral immune responses in vivo.

For culturing keratinocytes, cells are isolated from skin tissues and cultivated in EpiLife serum-free cell culture medium supplemented with human keratinocyte growth supplements (HKGS, Invitrogen, Carlsbad, CA) in the presence of proper antibiotics at 37° C. under 5% $CO_2$. Culture cells are passaged at 50%-60% confluency by exposing cells to trypsin/EDTA solution for 1 min and rinsing once with phenol red-free DMEM medium (Invitrogen), and the detached cells are replated at 1:10 dilution in fresh EpiLife medium with HKGS supplements. Human cancer and normal cell lines MCF7, HepG2, A549 and BEAS-2B were obtained either from the American Type Culture Collection (ATCC, Rockville, MD) or our collaborators and maintained according to manufacturer's suggestions. For RNA transfection, 0.5~500 µg of isolated mRNA (i.e. either 5hmRNA or mhmRNA) is dissolved in 0.5 ml of fresh EpiLife medium and mixed with 1~50 µl of In-VivoJetPEI transfection reagent. After 10~30 min incubation, the mixture is added into a cell culture containing 50%-60% confluency of the cultivated cells. The medium is reflashed every 12 to 48 hours, depending on cell types. This transfection procedure may be performed repeatedly to increase transfection efficiency. The transfection results are shown in FIG. 6 and FIG. 9, respectively.

2. Novel PCR-IVT Protocol

Figure 1:
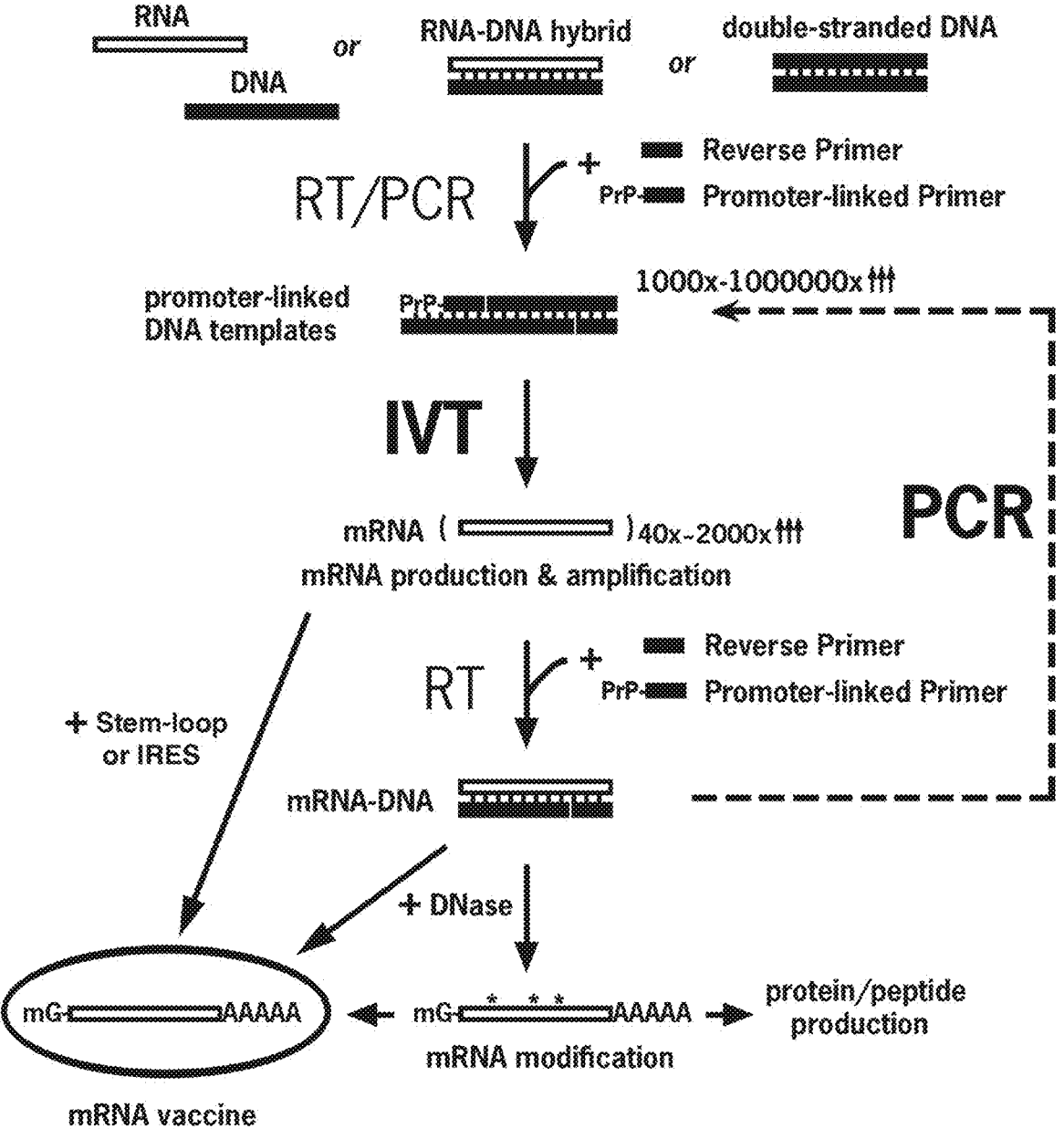
FIG. 1 depicts the step-by-step procedure of the PCR-IVT methodology. For mRNA production, a part or whole procedure of this PCR-IVT method can be adopted for either single or multiple cycle amplification of desired mRNA products.
Figure 2:
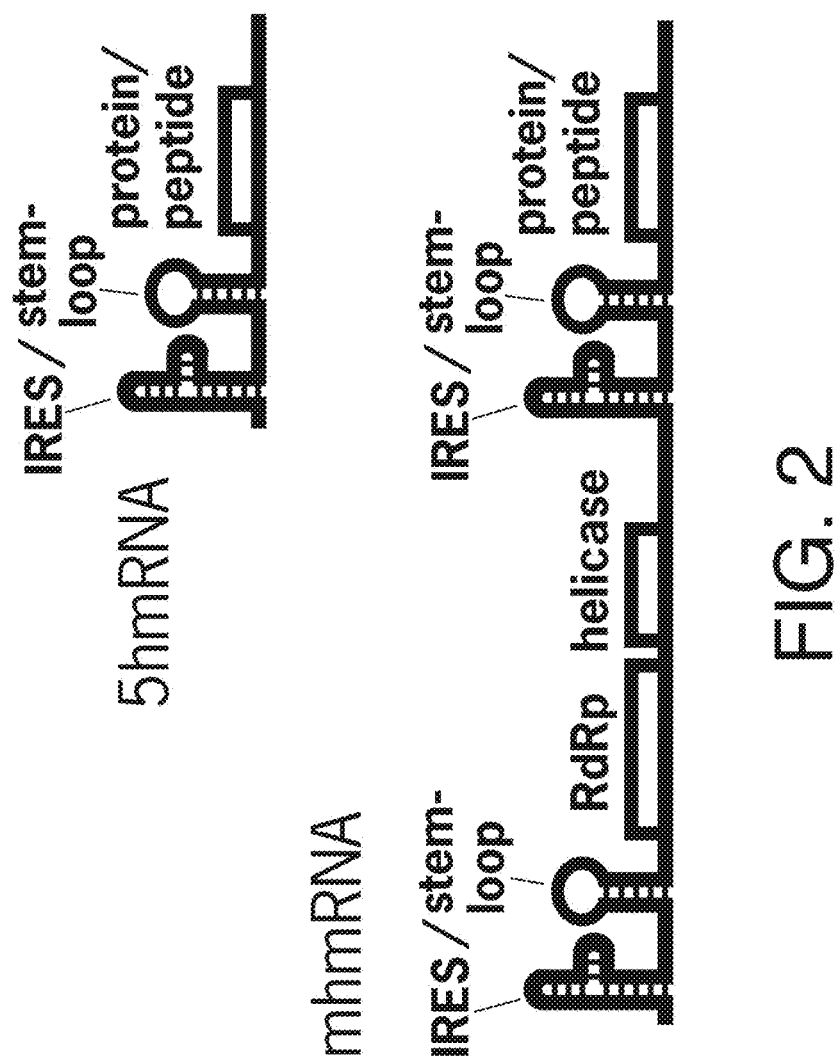
FIG. 2 depicts the designed structures of 5hmRNA and mhmRNA.
Figure 3:
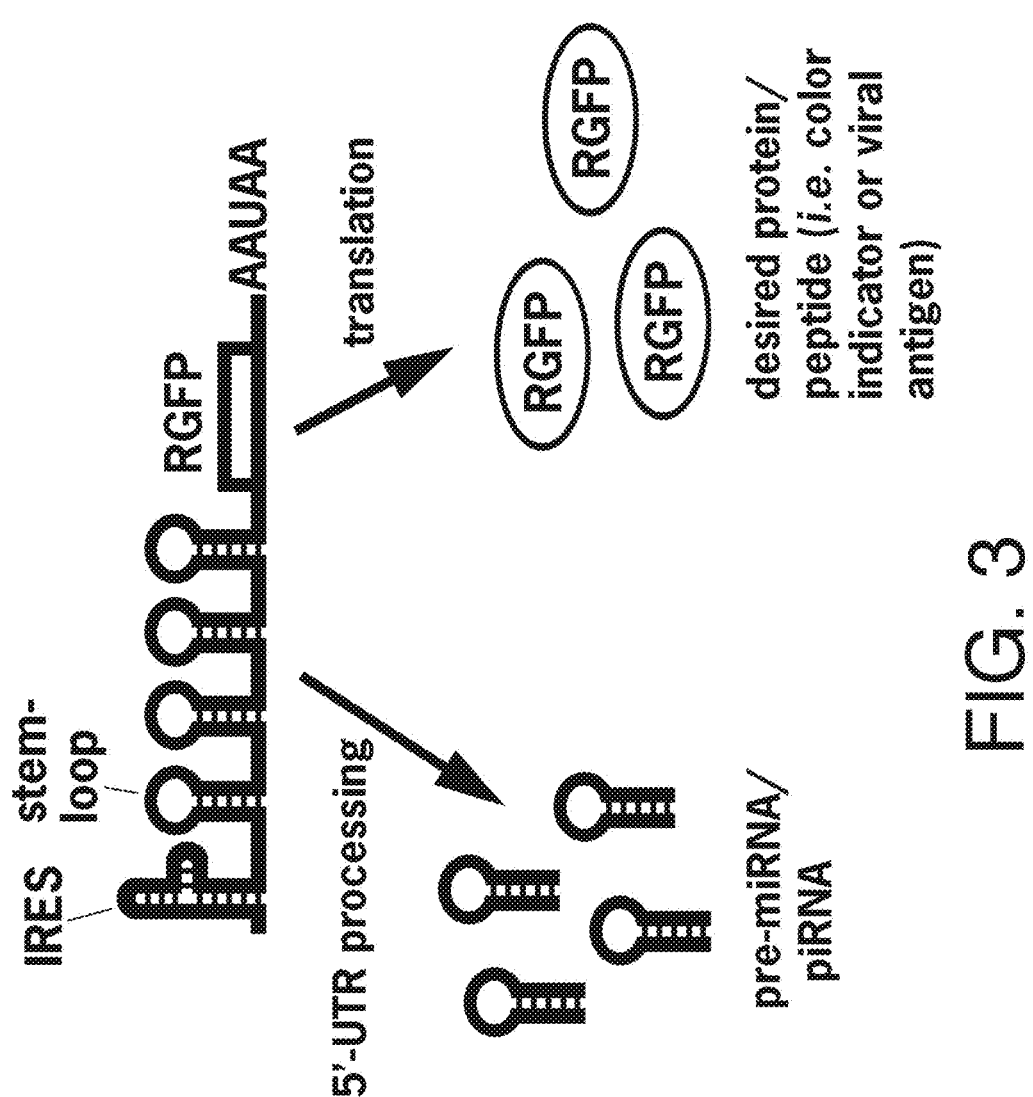
FIG. 3 depicts an example structure of designed red fluorescent RGFP-coding 5hmRNA. As shown, the stem-loop RNA structure of this RGFP-coding 5hmRNA contains a combination of SEQ.ID.NO.14/15, SEQ.ID.NO.3, SEQ.ID.NO.4, and SEQ.ID.NO.5 sequences located in the 5'-UTR of the encoded RGFP mRNA. Herein, just to serve as an example but not to limit the present invention, it is understandable that the stem-loop RNA structure can be replaced by any hairpin-like RNA, shRNA, pre-miRNA and/or IRES-like RNA structures for eliciting a desired biological effect or cellular function in vitro, ex vivo as well as in vivo. By the same token, the enconded RGFP mRNA can also be replaced by any other desired protein-/peptide-coding mRNA to eliciting at least a desired biological and/or cellular effect in vitro, ex vivo as well as in vivo, depending on the resulting protein/peptide function.

Reverse transcription (RT) of desired mRNA is performed by adding about 0.01 ng-10 microgram (µs) of isolated mRNA into a 20~50 µL RT reaction (SuperScript III RT kit, ThermoFisher Scientific, MA, USA), following the manufacturer's suggestions. Depending on the mRNA amount, the RT reaction mixture contains the mRNA, about 0.01~20 nmole RT primer, a proper amount of dNTPs and reverse transcriptase in 1×RT buffer. Then, the RT reaction is incubated at 46~65° C. for 1~3 hours (hr), depending on the structure and length of the desired mRNA, so as to make at least a complementary DNA (cDNA) template for the next step of PCR. Regarding RT primer designs, for serving as an example but not limited to this example, we use 5'-CAGTTCCAAT TGTGAAGATT CTC-3' (SEQ.ID.NO.16) for RT of a desired COVID-19 viral mRNA sequence and used another 5'-CTTGATGACG TTCTCAGTGC-3' (SEQ.ID.NO.17) for RT of another anti-cancer microRNA (miRNA) stem-loop-containing red fluorescent protein (RGFP)-coding mRNA (i.e. RGFP-coding 5hmRNA) of interest, respectively (FIG. 3).

Figure 4:
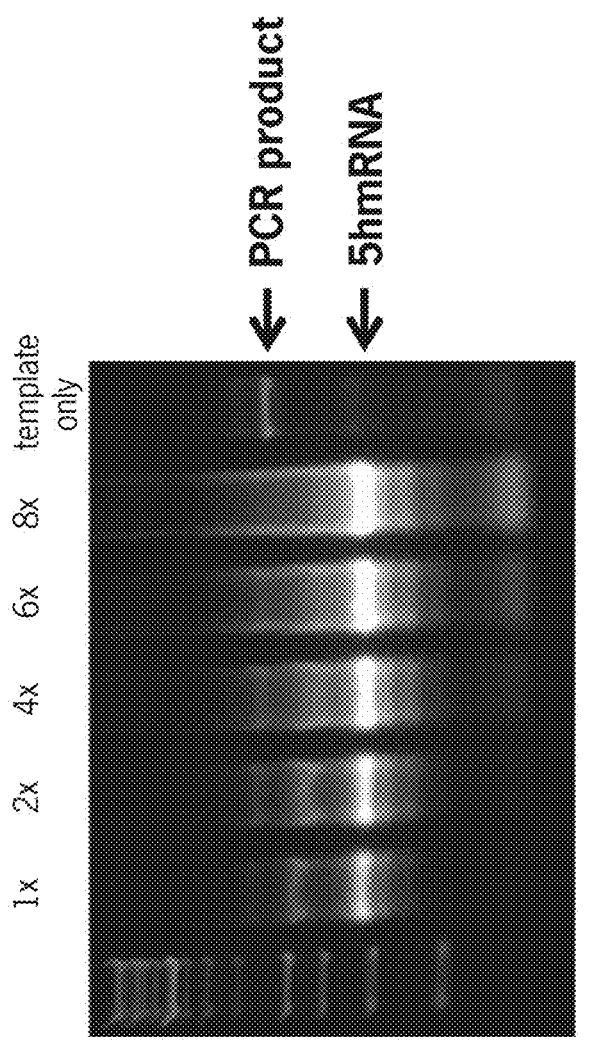
FIG. 4 shows the resulting promoter-incorporated PCR product and its derived 5hmRNA made by the invented PCR-IVT methodology with a novel helicase activity. Following an increase of starting amounts of the PCR product, the amplified 5hmRNA molecules are proportionally increased in a dose-dependent matter. Accordingly, an optimal generation rate of 30~2000 fold increase can be reached, resulting in a maximal up to 0.6~0.9 mg mRNA production per 1 mL IVT reaction (0.6~0.9 mg/mL mRNA).
Figure 5:
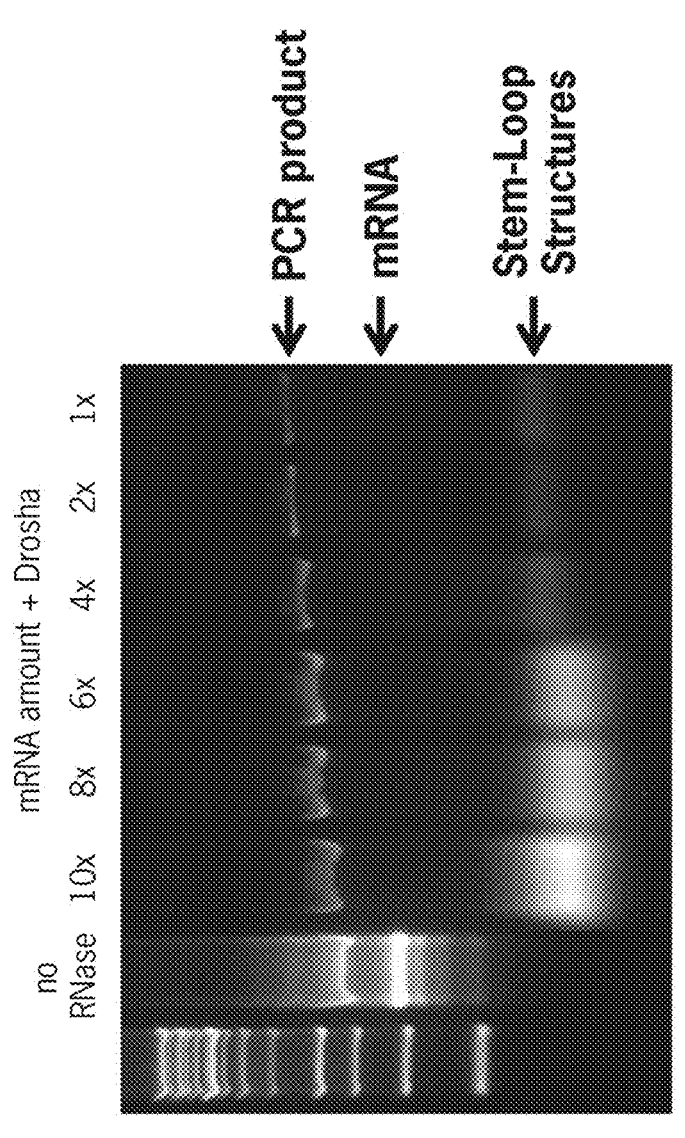
FIG. 5 shows the hairpin-like/IRES-like stem-loop RNA structures of PCR-IVT-made 5hmRNA (i.e. RGFP-coding 5hmRNA) sequences after processed by a Drosha-like RNaseIII enzyme activity (Ambion RNase III, ThermoFisher Scientific, MA, USA) in vitro. As shown in this example, the Drosha-processed hairpin-like RNA structures contain a designed IRES-like stem-loop RNA and precursors of miR-302b, miR-302c, and miR-302a. It is known that miR-302a, b and c are tumor-suppressor microRNAs, which are useful for anti-cancer therapy.
Figure 7:
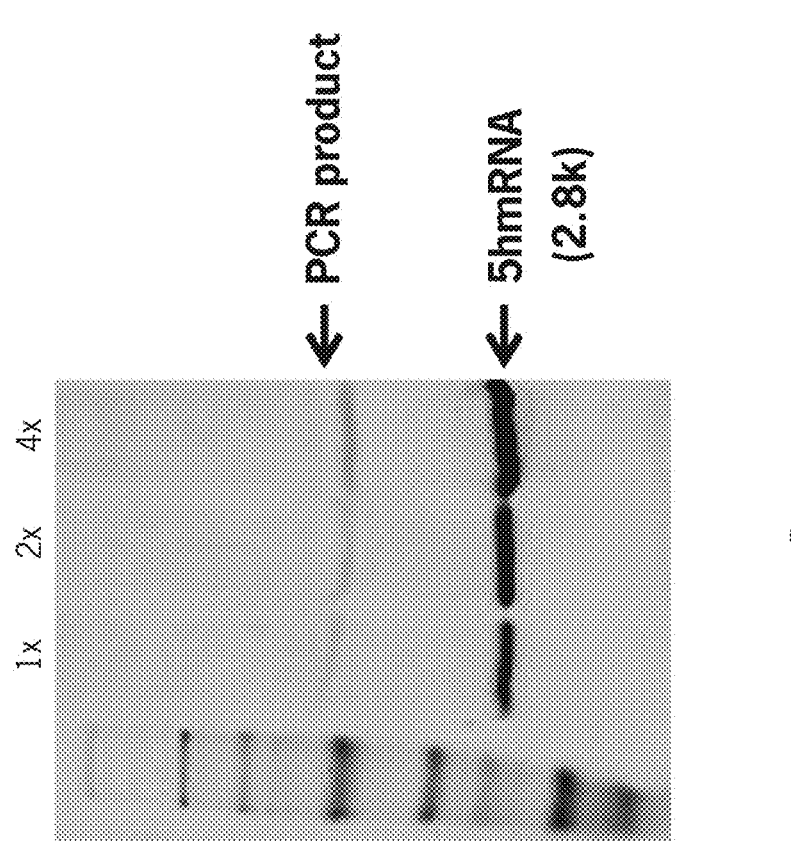
FIG. 7 shows Northern blot analysis result of anti-viral (COVID-19) 5hmRNA.
Figure 8:
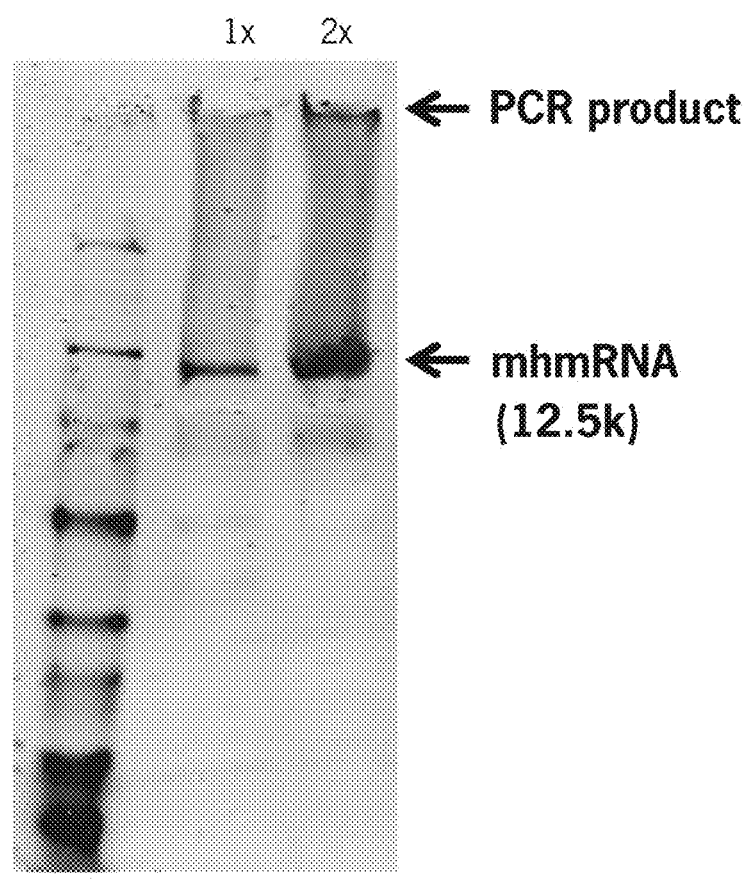
FIG. 8 shows Northern blot analysis result of anti-viral mhmRNA.

Next, polymerase chain reaction (PCR) is performed by adding about 0.01 pg~10 μg of the RT-derived cDNA into a 50 μL PCR mixture (High-Fidelity PCR Enzyme kit, ThermoFisher Scientific, MA, USA), following the manufacturer's suggestions. Then, the PCR mixture is first incubated in five to twenty (5~20) cycles of denaturation at 94° C. for 1 mim, annealing at 30~55° C. for 30 sec~1 min, and then extension at 72° C. for 1-3 min, depending on the structure and length of the desired DNA and primers. After that, another ten to twenty (10~20) cycles of PCR are performed with a series of sequential steps of denaturation at 94° C. for 1 mim, annealing at 50~55° C. for 30 sec, and then extension at 72° C. for 1~3 min, depending on the structure and length of the resulting PCR products. Finally, the resulting PCR products are used as templates for IVT. For serving as an example but not limited to this example, we have designed two sets of PCR pair primers for amplifying viral promoter-containing DNA templates, including a pair of 5'-GATATCTAAT ACGACTCACT ATAGGGAGAG GTATGGTACT TGGTAGTT-3' (SEQ.ID.NO.18) and SEQ.ID.NO.16 (for amplifying an about 12.5 k-nucleotide (nt) COVID-19 RdRp/helicase/S protein-coding mhmRNA (result shown in FIG. 8)) and another pair primers of 5'-GATATCTAAT ACGACTCACT ATAGGGAGAC TAGTGATGTT CTTGTTAACA ACT-3' (SEQ.ID.NO.19) and SEQ.ID.NO.16 (for amplifying an about 2.8 k-nt COVID-19 S 2 protein-coding 5hmRNA (result shown in FIG. 7)). Moreover, we use another pair of PCR primers for amplifying anti-cancer miRNA-stem-loop-containing RGFP-coding DNA templates (i.e. the RGFP-coding 5hmRNA), including a promoter-containing forward primer 5'-GATATCTAAT ACGACTCACT ATAGGGAGAG GTATGGTACT TGGTAGTT-3' (SEQ.ID.NO.20) and SEQ.ID.NO.17 (results shown in FIG. 4 and FIG. 5). In principal design, all designed forward PCR primers encode at least a conserved promoter sequence for IVT, such as, but not limited to T7, T3, and/or SP6 promoter sequences, particularly 5'-TCTAATACGA CTCACTATAG GGAGA-3' (SEQ.ID.NO.21). Furthermore, there may be at least a restriction site in the 3'-end of the forward promoter-primers for insertion of either at least a hairpin-like stem-loop structure or at least an IRES-like stem-loop structure in the PCR products.

For mRNA production, since a promoter-primer has been incorporated into the resulting PCR products, an improved IVT reaction can be performed to amplify desired mRNA sequences, using the PCR products as templates. The IVT reaction mixture contains 0.01 ng~10 μg of the PCR product, 0.1~10 U of helicase (Creative Enzymes, NY), a proper amount of NTPs and RNA polymerase (i.e. T7, T3, or SP6)

in 1× transcription buffer. The contents of 1× transcription buffer may be adjusted according to the used RNA polymerase, following the manufacturer's suggestions. Additionally, the 1× transcription buffer may further contain 0.001~10 mM of betaine (trimethylglycine, TMG), dimethylsulfoxide (DMSO), and/or 3-(N-morpholino)propane sulfonic acid (MOPS), and/or a combination thereof, which facilitates the denaturation of highly structured RNA/DNA sequences, such as hairpins and IRES. Then, the IVT reaction is incubated at 37° C. for 1~6 hr, depending on the stability and activity of the used RNA polymerase(s). In this improved novel IVT reaction, at least an additional helicase enzyme is added in order to facilitate the unwinding of RNA/DNA secondary structures, such as hairpin-like and IRES-like stem-loop structures, so as to overcome the low efficiency problem of hairpin-like RNA production in vitro. Notably, the helicase enzyme can unwind the secondary structures in both DNA and RNA strands.

3. RNA Purification, Northern Blot Analysis and RNA Sequencing

Desired mRNAs (10 μg) are isolated with a mirVana™ RNA isolation kit (Ambion, Austin, TX), following the manufacturer's protocol, and then further purified by using either 15% TBE-urea polyacrylamide gel or 3.5% low melting point agarose gel electrophoresis. For Northern blot analysis, the gel-fractionated mRNAs are electroblotted onto a nylon membrane. Detection of the mRNA and its IVT template (the PCR product) is performed with a labeled [LNA]-DNA probe complementary to a desired target sequence of the mRNA. The probe is further purified by high-performance liquid chromatography (HPLC) and tail-labeled with terminal transferase (20 units) for 20 min in the presence of either a dye-labeled nucleotide analog or [$^{32}$P]-dATP (>3000 Ci/mM, Amersham International, Arlington Heights, IL). For determining mRNA/miRNA sequences, the designed SEQ.ID.NO.21 and either SEQ.ID.NO.16 or SEQ.ID.NO.17 are used as primers, separately, for performing RNA sequencing from the 5'-end and 3'-end of the mRNA/miRNA sequences, respectively.

4. Protein Extraction and Western Blot Analysis

Cells ($10^6$) are lysed with a CelLytic-M lysis/extraction reagent (Sigma) supplemented with protease inhibitors, Leupeptin, TLCK, TAME and PMSF, following the manufacturer's suggestion. Lysates are centrifuged at 12,000 rpm for 20 min at 4° C. and the supernatant is recovered. Protein concentrations are measured using an improved SOFTmax protein assay package on an E-max microplate reader (Molecular Devices, CA). Each 30 μg of cell lysate are added to SDS-PAGE sample buffer under reducing (+50 mM DTT) and non-reducing (no DTT) conditions, and boiled for 3 min before loading onto a 6-8% polyacrylamide gel. Proteins are resolved by SDS-polyacrylamide gel electrophoresis (PAGE), electroblotted onto a nitrocellulose membrane and incubated in Odyssey blocking reagent (Li-Cor Biosciences, Lincoln, NB) for 2 hr at room temperature. Then, a primary antibody is applied to the reagent and incubated the mixture at 4° C. After overnight incubation, the membrane is rinsed three times with TBS-T and then exposed to goat anti-mouse IgG conjugated secondary antibody to Alexa Fluor 680 reactive dye (1:2,000; Invitrogen—Molecular Probes), for 1 hr at the room temperature. After three additional TBS-T rinses, fluorescent scanning of the immunoblot and image analysis are conducted using Li-Cor Odyssey Infrared Imager and Odyssey Software v.10 (Li-Cor).

5. Immunostaining Assay

Cell/Tissue samples are fixed in 100% methanol for 30 min at 4° C. and then 4% paraformaldehyde (in 1×PBS, pH 7.4) for 10 min at 20° C. After that, the samples are incubated in 1×PBS containing 0.1-0.25% Triton X-100 for 10 min and then washed in 1×PBS three times for 5 min. For immunostaining, primary antibodies include, but not limited to, anti-DsRed/RGFP (Clontech, Palo Alto, CA) and anti-COVID-19 S (Invitrogen) monoclonal antibodies. Dye-labeled goat anti-rabbit or horse anti-mouse antibody are used as the secondary antibody (Invitrogen—Molecular Probes, Carlsbad, CA). Results are examined and analyzed at 100× or 200× magnification under a fluorescent 80i microscopic quantitation system with a Metamorph imaging program (Nikon). Positive results are shown in FIG. 6 and FIG. 9.

6. In Vivo Transfection Assay

Isolated mRNA or miRNA from Examples 2 and 3 is mixed well with a proper amount of delivery agent, such as an In-VivoJetPEI transfection reagent, following the manufacturer's protocol, and then injected into blood veins or muscles of an animal, depending the purpose of applications. The delivery agent is used for mixing, conjugating, encapsulating or formulating the desired 5hmRNA or mhmRNA, so as to not only protect the 5hmRNA or mhmRNA from degradation but also facilitate the delivery of the 5hmRNA or mhmRNA into specific target cells of interest in vitro, ex vivo and/or in vivo.

7. Statistic Analysis

Any change over 75% of signal intensity in the analyses of immunostaining, western blotting and northern blotting is considered as a positive result, which in turn is analyzed and presented as mean±SE. Statistical analysis of data is performed by one-way ANOVA. When main effects are significant, the Dunnett's post-hoc test is used to identify the groups that differ significantly from the controls. For pairwise comparison between two treatment groups, the two-tailed student t test is used. For experiments involving more than two treatment groups, ANOVA is performed followed by a post-hoc multiple range test. Probability values of $p<0.05$ is considered significant. All p values are determined from two-tailed tests.

REFERENCES

1. U.S. Pat. No. 7,662,791 to Shi-Lung Lin et al.
2. U.S. Pat. No. 8,080,652 to Shi-Lung Lin et al.
3. U.S. Pat. No. 8,372,969 to Ying S Y and Shi-Lung Lin.
4. U.S. Pat. No. 8,609,831 to Shi-Lung Lin and Ying S Y.
5. U.S. Pat. No. 9,637,747 to Shi-Lung Lin et al.
6. U.S. Pat. No. 9,783,811 to Shi-Lung Lin et al.
7. U.S. Provisional Patent Application No. 60/222,479 to Shi-Lung Lin.
8. U.S. Provisional Patent Application No. 60/290,902 to Shi-Lung Lin.
9. Shi-Lung Lin and Ji H; Replicase cycling reaction amplification. WO2002/092774.
10. Shi-Lung Lin; Peptide library construction from RNA-PCR-derived RNAs. *Methods Mol Biol.* 221:289-293, 2003.
11. Shi-Lung Lin and Ji H; cDNA library construction using in-vitro transcriptional amplification. *Methods Mol Biol.* 221:93-101, 2003.
12. McDowell et al.; Determination of intrinsic transcription termination efficiency by RNA polymerase elongation rate. *Science* 266:822-825, 1994.
13. Schlake et al.; Developing mRNA-Vaccine Technologies. *RNA biology* 9:1319-1330, 2012.
14. Ko et al.; Development of an RNA Expression Platform Controlled by Viral Internal Ribosome Entry Sites. *J. Micobiol. Biotechnol.* 29:127-140, 2019.

SEQUENCE LISTING (1) GENERAL INFORMATION:
   (iii) NUMBER OF SEQUENCES: 21
(2) INFORMATION FOR SEQ ID NO:1:
   (i) SEQUENCE CHARACTERISTICS:
     (A) LENGTH: 6 base pairs
     (B) TYPE: nucleic acid
     (C) STRANDEDNESS: single
     (D) TOPOLOGY: linear
   (ii) MOLECULE TYPE: RNA
     (A) DESCRIPTION: /desc="synthetic"
   (iii) HYPOTHETICAL: NO
   (iv) ANTI-SENSE: NO
   (xi) SEQUENCE DESCRIPTION: SEQ ID NO:1:
     AAUAAA
(2) INFORMATION FOR SEQ ID NO:2:
   (i) SEQUENCE CHARACTERISTICS:
     (A) LENGTH: 7 base pairs
     (B) TYPE: nucleic acid
     (C) STRANDEDNESS: single
     (D) TOPOLOGY: linear
   (ii) MOLECULE TYPE: RNA
     (A) DESCRIPTION: /desc="synthetic"
   (iii) HYPOTHETICAL: NO
   (iv) ANTI-SENSE: NO
   (xi) SEQUENCE DESCRIPTION: SEQ ID NO:2:
     AAUUAAA
(2) INFORMATION FOR SEQ ID NO:3:
   (i) SEQUENCE CHARACTERISTICS:
     (A) LENGTH: 73 base pairs
     (B) TYPE: nucleic acid
     (C) STRANDEDNESS: single
     (D) TOPOLOGY: hairpin
   (ii) MOLECULE TYPE: RNA
     (A) DESCRIPTION: /desc="synthetic"
   (iii) HYPOTHETICAL: NO
   (iv) ANTI-SENSE: NO
   (xi) SEQUENCE DESCRIPTION: SEQ ID NO:3:
     GCUCCCUUCA ACUUUAACAU GGAAGUGCUU UCUGUGACUU UAAAAGUAAG UGCUUCCAUG UUUUAGUAGG AGU 73
(2) INFORMATION FOR SEQ ID NO:4:
   (i) SEQUENCE CHARACTERISTICS:
     (A) LENGTH: 68 base pairs
     (B) TYPE: nucleic acid
     (C) STRANDEDNESS: single
     (D) TOPOLOGY: hairpin
   (ii) MOLECULE TYPE: RNA
     (A) DESCRIPTION: /desc="synthetic"
   (iii) HYPOTHETICAL: NO
   (iv) ANTI-SENSE: NO
   (xi) SEQUENCE DESCRIPTION: SEQ ID NO:4:
     CCUUUGCUUU AACAUGGGGG UACCUGCUGU GUGAAACAAA AGUAAGUGCU UCCAUGUUUC AGUGGAGG 68
(2) INFORMATION FOR SEQ ID NO:5:
   (i) SEQUENCE CHARACTERISTICS:
     (A) LENGTH: 69 base pairs
     (B) TYPE: nucleic acid
     (C) STRANDEDNESS: single
     (D) TOPOLOGY: hairpin (ii) MOLECULE TYPE: RNA (A) DESCRIPTION: /desc="synthetic"

(iii) HYPOTHETICAL: NO (iv) ANTI-SENSE: NO (xi) SEQUENCE DESCRIPTION: SEQ ID NO:5:
CCACCACUUA AACGUGGAUG UACUUGC-
UUU GAAACUAAAG AAGUAAGUGC UUC-
CAUGUU UUGGUGAUGG 69

(2) INFORMATION FOR SEQ ID NO:6:

(i) SEQUENCE CHARACTERISTICS:

(A) LENGTH: 68 base pairs (B) TYPE: nucleic acid (C) STRANDEDNESS: single (D) TOPOLOGY: hairpin (ii) MOLECULE TYPE: RNA (A) DESCRIPTION: /desc="synthetic"

(iii) HYPOTHETICAL: NO (iv) ANTI-SENSE: NO (xi) SEQUENCE DESCRIPTION: SEQ ID NO:6:
CCUCUACUUU AACAUGGAGG CAC-
UUGCUGU GACAUGACAA AAAUAAGUGC
UUCCAUGUUU GAGUGUGG 68

(2) INFORMATION FOR SEQ ID NO:7:

(i) SEQUENCE CHARACTERISTICS:

(A) LENGTH: 44 base pairs (B) TYPE: nucleic acid (C) STRANDEDNESS: single (D) TOPOLOGY: stem-loop (ii) MOLECULE TYPE: RNA (A) DESCRIPTION: /desc="synthetic"

(iii) HYPOTHETICAL: NO (iv) ANTI-SENSE: NO (xi) SEQUENCE DESCRIPTION: SEQ ID NO:7:
CUGUGUGGCU GUCACUCGGC UGCAUGC-
UUA GUGCACUCAC GCAG 44

(2) INFORMATION FOR SEQ ID NO:8:

(i) SEQUENCE CHARACTERISTICS:

(A) LENGTH: 65 base pairs (B) TYPE: nucleic acid (C) STRANDEDNESS: single (D) TOPOLOGY: stem-loop (ii) MOLECULE TYPE: RNA (A) DESCRIPTION: /desc="synthetic"

(iii) HYPOTHETICAL: NO (iv) ANTI-SENSE: NO (xi) SEQUENCE DESCRIPTION: SEQ ID NO:8:
CUGUGUGGCU GUCACUCGGC UGCAUGC-
UUA GUGCACUCAC GCAGUAUAAU
UAAUAACUAA UUACU (2) INFORMATION FOR SEQ ID NO:9:

(i) SEQUENCE CHARACTERISTICS:

(A) LENGTH: 147 base pairs (B) TYPE: nucleic acid (C) STRANDEDNESS: single (D) TOPOLOGY: stem-loop (ii) MOLECULE TYPE: RNA (A) DESCRIPTION: /desc="synthetic"

(iii) HYPOTHETICAL: NO (iv) ANTI-SENSE: NO (xi) SEQUENCE DESCRIPTION: SEQ ID NO:9:
GUCGUUGACA GGACACGAGU AACUCGU-
CUA UCUUCUGCAG GCUGCUUACG GUUUC-
GUCCG UGUUGCAGCC GAUCAUCAGC
ACAUCUAGGU UUCGUCCGGG
UGUGACCGAA AGGUAAGAUG GAGAGCC-
UUG UCCCUGGUUU CAACGAG (2) INFORMATION FOR SEQ ID NO:10:

(i) SEQUENCE CHARACTERISTICS:

(A) LENGTH: 88 base pairs (B) TYPE: nucleic acid (C) STRANDEDNESS: single (D) TOPOLOGY: stem-loop (ii) MOLECULE TYPE: RNA (A) DESCRIPTION: /desc="synthetic"

(iii) HYPOTHETICAL: NO (iv) ANTI-SENSE: NO (xi) SEQUENCE DESCRIPTION: SEQ ID NO:10:
AAUUAUAAAU UACCAGAUGA UUUUA-
CAGGC UGCGUUAUAG CUUGGAAUUC
UAACAAUCUU GAUUCUAAGG UUGGUG-
GUAA UUAUAAUU (2) INFORMATION FOR SEQ ID NO:11:

(i) SEQUENCE CHARACTERISTICS:

(A) LENGTH: 129 base pairs (B) TYPE: nucleic acid (C) STRANDEDNESS: single (D) TOPOLOGY: multiple stem-loop (ii) MOLECULE TYPE: RNA (A) DESCRIPTION: /desc="synthetic"

(iii) HYPOTHETICAL: NO (iv) ANTI-SENSE: NO (xi) SEQUENCE DESCRIPTION: SEQ ID NO:11:
CACAAAUAUU ACCAGAUCCA UCAAAAC-
CAA GCAAGAGGUC AUUUAUUGAA GAUC-
UACUUU UCAACAAAGU GACACUUGCA
GAUGCUGGCU UCAUCAAACA AUAUG-
GUGAU UGCCUUGGUG AUAUUGCUG (2) INFORMATION FOR SEQ ID NO:12:

(i) SEQUENCE CHARACTERISTICS:

(A) LENGTH: 189 base pairs (B) TYPE: nucleic acid (C) STRANDEDNESS: single (D) TOPOLOGY: multiple stem-loop (ii) MOLECULE TYPE: RNA (A) DESCRIPTION: /desc="synthetic"

(iii) HYPOTHETICAL: NO (iv) ANTI-SENSE: NO (xi) SEQUENCE DESCRIPTION: SEQ ID NO:12:
GCAAAAAUGU GAUCUUGCUU GUAAAUA-
CAA UUUUUGAGAGG UUAAUAAAUU ACA-
AGUAGUG CUAUUUUUGU AUUUAGGUUA
GCUAUUUAGC UUUACGUUCC AGGAUGC-
CUA GUGGCAGCCC CACAAUAUCC
AGGAAGCCCU CUCUGCGGUU
UUUCAGAUUC GUUAGUCGAA AAACC-
UAAGA AAUUUAAUG (2) INFORMATION FOR SEQ ID NO:13:

(i) SEQUENCE CHARACTERISTICS:

(A) LENGTH: 294 base pairs (B) TYPE: nucleic acid (C) STRANDEDNESS: single (D) TOPOLOGY: multiple stem-loop (ii) MOLECULE TYPE: RNA (A) DESCRIPTION: /desc="synthetic"

(iii) HYPOTHETICAL: NO (iv) ANTI-SENSE: NO (xi) SEQUENCE DESCRIPTION: SEQ ID NO:13:
CACUCCCCUG UGAGGACUAC UGUCUU-
CACG CAGAAAGCGU CUAGCCAUGG CGUU-
AGUAUG AGUGUCGUGC AGCCUCCAGG
ACCCCCCCUC CCGGGAGAGC CAUAGUG-
GUC UGCGGAACCG GUGAGUACAC
CGGAAUUGCC AGGACGACCG GGUCC- UUUCU UGGAUCAACC CGCUCAAUGC CUG-GAGAUUU GGGCGUGCCC CCGCGAGACU GCUAGCCGAG UAGUGUUGGG UCGCGAAAGG CCUUGUGGUA CUGC-CUGAUG GGUGCUUGCG AGUGCCCCGG GAGGUCUCGU AGAC 294

(2) INFORMATION FOR SEQ ID NO:14:

(i) SEQUENCE CHARACTERISTICS:

(A) LENGTH: 55 base pairs (B) TYPE: nucleic acid (C) STRANDEDNESS: single (D) TOPOLOGY: stem-loop (ii) MOLECULE TYPE: RNA (A) DESCRIPTION: /desc="synthetic"

(iii) HYPOTHETICAL: NO (iv) ANTI-SENSE: NO (xi) SEQUENCE DESCRIPTION: SEQ ID NO:14:
    GGACACGAGU AACUCGUCUA UCUUCUGCAG GCUGCUUACG GUUUCGU-CCG UGUUG 55

(2) INFORMATION FOR SEQ ID NO:15:

(i) SEQUENCE CHARACTERISTICS:

(A) LENGTH: 52 base pairs (B) TYPE: nucleic acid (C) STRANDEDNESS: single (D) TOPOLOGY: stem-loop (ii) MOLECULE TYPE: RNA (A) DESCRIPTION: /desc="synthetic"

(iii) HYPOTHETICAL: NO (iv) ANTI-SENSE: NO (xi) SEQUENCE DESCRIPTION: SEQ ID NO:15:
    CAGCCGAUCA UCAGCACAUC UAG-GUUUUGU CCGGGUGUGA CCGAAAGGUA AG 52

(2) INFORMATION FOR SEQ ID NO:16:

(i) SEQUENCE CHARACTERISTICS:

(A) LENGTH: 23 base pairs (B) TYPE: nucleic acid (C) STRANDEDNESS: single (D) TOPOLOGY: linear (ii) MOLECULE TYPE: DNA (A) DESCRIPTION: /desc="synthetic"

(iii) HYPOTHETICAL: NO (iv) ANTI-SENSE: YES (xi) SEQUENCE DESCRIPTION: SEQ ID NO:16:
    CAGTTCCAAT TGTGAAGATT CTC (2) INFORMATION FOR SEQ ID NO:17:

(i) SEQUENCE CHARACTERISTICS:

(A) LENGTH: 20 base pairs (B) TYPE: nucleic acid (C) STRANDEDNESS: single (D) TOPOLOGY: linear (ii) MOLECULE TYPE: DNA (A) DESCRIPTION: /desc="synthetic"

(iii) HYPOTHETICAL: NO (iv) ANTI-SENSE: YES (xi) SEQUENCE DESCRIPTION: SEQ ID NO:17:
    CTTGATGACG TTCTCAGTGC (2) INFORMATION FOR SEQ ID NO:18:

(i) SEQUENCE CHARACTERISTICS:

(A) LENGTH: 48 base pairs (B) TYPE: nucleic acid (C) STRANDEDNESS: single (D) TOPOLOGY: linear (ii) MOLECULE TYPE: DNA (A) DESCRIPTION: /desc="synthetic"

(iii) HYPOTHETICAL: NO (iv) ANTI-SENSE: NO (xi) SEQUENCE DESCRIPTION: SEQ ID NO:18:
    GATATCTAAT ACGACTCACT ATAGGGAGAG GTATGGTACT TGGTAGTT 48

(2) INFORMATION FOR SEQ ID NO:19:

(i) SEQUENCE CHARACTERISTICS:

(A) LENGTH: 53 base pairs (B) TYPE: nucleic acid (C) STRANDEDNESS: single (D) TOPOLOGY: linear (ii) MOLECULE TYPE: DNA (A) DESCRIPTION: /desc="synthetic"

(iii) HYPOTHETICAL: NO (iv) ANTI-SENSE: NO (xi) SEQUENCE DESCRIPTION: SEQ ID NO:19:
    GATATCTAAT ACGACTCACT ATAGGGAGAC TAGTGATGTT CTTGTTAACA ACT 53

(2) INFORMATION FOR SEQ ID NO:20:

(i) SEQUENCE CHARACTERISTICS:

(A) LENGTH: 48 base pairs (B) TYPE: nucleic acid (C) STRANDEDNESS: single (D) TOPOLOGY: linear (ii) MOLECULE TYPE: DNA (A) DESCRIPTION: /desc="synthetic"

(iii) HYPOTHETICAL: NO (iv) ANTI-SENSE: NO (xi) SEQUENCE DESCRIPTION: SEQ ID NO:20:
    GATATCTAAT ACGACTCACT ATAGGGAGAG GTATGGTACT TGGTAGTT 48

(2) INFORMATION FOR SEQ ID NO:21:

(i) SEQUENCE CHARACTERISTICS:

(A) LENGTH: 25 base pairs (B) TYPE: nucleic acid (C) STRANDEDNESS: single (D) TOPOLOGY: linear (ii) MOLECULE TYPE: DNA (A) DESCRIPTION: /desc="synthetic"

(iii) HYPOTHETICAL: NO (iv) ANTI-SENSE: NO (xi) SEQUENCE DESCRIPTION: SEQ ID NO:21:
    TCTAATACGA CTCACTATAG GGAGA

---

SEQUENCE LISTING

<160> NUMBER OF SEQ ID NOS: 21

<210> SEQ ID NO 1
<211> LENGTH: 6
<212> TYPE: RNA
<213> ORGANISM: Artificial Sequence
<220> FEATURE:
<223> OTHER INFORMATION: Synthetic -continued

```
<400> SEQUENCE: 1 aauaaa                                                              6

<210> SEQ ID NO 2
<211> LENGTH: 7
<212> TYPE: RNA
<213> ORGANISM: Artificial Sequence
<220> FEATURE:
<223> OTHER INFORMATION: Synthetic

<400> SEQUENCE: 2 aauuaaa                                                             7

<210> SEQ ID NO 3
<211> LENGTH: 73
<212> TYPE: RNA
<213> ORGANISM: Artificial Sequence
<220> FEATURE:
<223> OTHER INFORMATION: Synthetic

<400> SEQUENCE: 3
gcucccuuca acuuuaacau ggaagugcuu ucgugacuu uaaaaguaag ugcuuccaug    60
uuuuaguagg agu                                                      73

<210> SEQ ID NO 4
<211> LENGTH: 68
<212> TYPE: RNA
<213> ORGANISM: Artificial Sequence
<220> FEATURE:
<223> OTHER INFORMATION: Synthetic

<400> SEQUENCE: 4
ccuuugcuuu aacauggggg uaccugcugu gugaaacaaa aguaagugcu uccauguuuc    60
aguggagg                                                            68

<210> SEQ ID NO 5
<211> LENGTH: 69
<212> TYPE: RNA
<213> ORGANISM: Artificial Sequence
<220> FEATURE:
<223> OTHER INFORMATION: Synthetic

<400> SEQUENCE: 5
ccaccacuua aacguggaug uacuugcuuu gaaacuaaag aaguaagugc uuccauguuu    60
uggugaugg                                                           69

<210> SEQ ID NO 6
<211> LENGTH: 68
<212> TYPE: RNA
<213> ORGANISM: Artificial Sequence
<220> FEATURE:
<223> OTHER INFORMATION: Synthetic

<400> SEQUENCE: 6
ccucuacuuu aacauggagg cacuugcugu gacaugacaa aaauaagugc uuccauguuu    60
gagugugg                                                            68

<210> SEQ ID NO 7
<211> LENGTH: 44
<212> TYPE: RNA
<213> ORGANISM: Artificial Sequence
<220> FEATURE:
<223> OTHER INFORMATION: Synthetic
```

```
<400> SEQUENCE: 7
cuguguggcu gucacucggc ugcaugcuua gugcacucac gcag                        44

<210> SEQ ID NO 8
<211> LENGTH: 65
<212> TYPE: RNA
<213> ORGANISM: Artificial Sequence
<220> FEATURE:
<223> OTHER INFORMATION: Synthetic

<400> SEQUENCE: 8
cuguguggcu gucacucggc ugcaugcuua gugcacucac gcaguauaau uaauaacuaa       60
uuacu                                                                  65

<210> SEQ ID NO 9
<211> LENGTH: 147
<212> TYPE: RNA
<213> ORGANISM: Artificial Sequence
<220> FEATURE:
<223> OTHER INFORMATION: Synthetic

<400> SEQUENCE: 9
gucguugaca ggacacgagu aacucgucua ucuucugcag gcugcuuacg guuucguccg       60
uguugcagcc gaucaucagc acaucuaggu uucguccggg ugugaccgaa agguaagaug      120
gagagccuug ucccugguuu caacgag                                         147

<210> SEQ ID NO 10
<211> LENGTH: 88
<212> TYPE: RNA
<213> ORGANISM: Artificial Sequence
<220> FEATURE:
<223> OTHER INFORMATION: Synthetic

<400> SEQUENCE: 10
aauuauaaau uaccagauga uuuuacaggc ugcguuauag cuuggaauuc uaacaaucuu       60
gauucuaagg uuggugguaa uuauaauu                                         88

<210> SEQ ID NO 11
<211> LENGTH: 129
<212> TYPE: RNA
<213> ORGANISM: Artificial Sequence
<220> FEATURE:
<223> OTHER INFORMATION: Synthetic

<400> SEQUENCE: 11
cacaaauauu accagaucca ucaaaaccaa gcaagagguc auuuauugaa gaucuacuuu       60
ucaacaaagu gacacuugca gaugcuggcu ucaucaaaca auauggugau ugccuuggug      120
auauugcug                                                             129

<210> SEQ ID NO 12
<211> LENGTH: 189
<212> TYPE: RNA
<213> ORGANISM: Artificial Sequence
<220> FEATURE:
<223> OTHER INFORMATION: Synthetic

<400> SEQUENCE: 12
gcaaaaaugu gaucuugcuu guaaauacaa uuuugagagg uuaauaaauu acaaguagug       60
cuauuuuugu auuuagguua gcuauuuagc uuuacguucc aggaugccua guggcagccc      120
```

-continued cacaauauucc aggaagcccu cucugcgguu uuucagauuc guuagucgaa aaaccuaaga          180
aauuuaaug                                                                   189

<210> SEQ ID NO 13
<211> LENGTH: 294
<212> TYPE: RNA
<213> ORGANISM: Artificial Sequence
<220> FEATURE:
<223> OTHER INFORMATION: Synthetic

<400> SEQUENCE: 13 cacucccug ugaggacuac ugucuucacg cagaaagcgu cuagccaugg cguuaguaug           60
agugucgugc agccuccagg accccccuc ccgggagagc cauagugguc ugcggaaccg          120
gugaguacac cggaauugcc aggacgaccg gguccuuucu uggaucaacc cgcucaaugc         180
cuggagauuu gggcgugccc ccgcgagacu gcuagccgag uaguguuggg ucgcgaaagg         240
ccuuguggua cugccugaug ggugcuugcg agugccccgg gaggucucgu agac              294

<210> SEQ ID NO 14
<211> LENGTH: 55
<212> TYPE: RNA
<213> ORGANISM: Artificial Sequence
<220> FEATURE:
<223> OTHER INFORMATION: Synthetic

<400> SEQUENCE: 14
ggacacgagu aacucgucua ucuucugcag gcugcuuacg guuucguccg uguug              55

<210> SEQ ID NO 15
<211> LENGTH: 52
<212> TYPE: RNA
<213> ORGANISM: Artificial Sequence
<220> FEATURE:
<223> OTHER INFORMATION: Synthetic

<400> SEQUENCE: 15
cagccgauca ucagcacauc uagguuuugu ccggguguga ccgaaaggua ag                 52

<210> SEQ ID NO 16
<211> LENGTH: 23
<212> TYPE: DNA
<213> ORGANISM: Artificial Sequence
<220> FEATURE:
<223> OTHER INFORMATION: Synthetic

<400> SEQUENCE: 16
cagttccaat tgtgaagatt ctc                                                  23

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
cttgatgacg ttctcagtgc                                                      20

<210> SEQ ID NO 18
<211> LENGTH: 48
<212> TYPE: DNA
<213> ORGANISM: Artificial Sequence
<220> FEATURE:
<223> OTHER INFORMATION: Synthetic

```
<400> SEQUENCE: 18
gatatctaat acgactcact atagggagag gtatggtact tggtagtt                    48

<210> SEQ ID NO 19
<211> LENGTH: 53
<212> TYPE: DNA
<213> ORGANISM: Artificial Sequence
<220> FEATURE:
<223> OTHER INFORMATION: Synthetic

<400> SEQUENCE: 19
gatatctaat acgactcact atagggagac tagtgatgtt cttgttaaca act            53

<210> SEQ ID NO 20
<211> LENGTH: 48
<212> TYPE: DNA
<213> ORGANISM: Artificial Sequence
<220> FEATURE:
<223> OTHER INFORMATION: Synthetic

<400> SEQUENCE: 20
gatatctaat acgactcact atagggagag gtatggtact tggtagtt                    48

<210> SEQ ID NO 21
<211> LENGTH: 25
<212> TYPE: DNA
<213> ORGANISM: Artificial Sequence
<220> FEATURE:
<223> OTHER INFORMATION: Synthetic

<400> SEQUENCE: 21
tctaatacga ctcactatag ggaga                                            25
```

The invention claimed is:

1. A production method for manufacturing and amplifying self-amplifiable RNA construct exhibiting additional helicase activity, comprising:

(a) providing at least a DNA template encoding at least an RNA sequence, wherein a product of transcription of the RNA sequence is a messenger-hairpin-messenger RNA (mhmRNA) construct the mhmRNA construct contains at least a stem-loop RNA structure flanked with two different mRNA sequences of interest on its both sides comprising a first 5'-mRNA and a second 3'-mRNA, and wherein the first 5'-mRNA encodes COVID-19 virus RdRp, which consists solely of Nsp12, Nsp8, and Nsp7 and exhibits both RNA replicase activity and additional helicase activity, thereby contributing to the self-amplifiability of the mhmRNA construct;

(b) providing an in-vitro transcription (IVT) reaction condition containing NTPs, a preset buffer system, and at least a DNA-dependent RNA polymerase; and said preset buffer system contains chemicals to facilitate the denaturation of highly structured RNA/DNA sequences;

(c) mixing the DNA template of (a) and the IVT reaction condition of (b) to generate and amplify the mhmRNA construct from the encoded RNA sequence, wherein the stem-loop RNA structure of said mhmRNA construct contains at least a sequence selected from SEQ.ID.NO.3, SEQ.ID.NO.4, SEQ.ID.NO.5, SEQ.ID.NO.6, SEQ.ID.NO.7, SEQ.ID.NO.8, SEQ.ID.NO.9, SEQ.ID.NO.10, SEQ.ID.NO.11, SEQ.ID.NO.12, SEQ.ID.NO.13, SEQ.ID.NO.14, SEQ.ID.NO.15, and a combination thereof.

2. The production method as defined in claim 1, wherein said stem-loop RNA structure contains at least a perfectly or imperfectly matched either single or multiple hairpin structure, ranging about 10~800 nucleotides in length, and said-mhmRNA construct further comprises a short sequence located between the stem-loop RNA structure and a start codon of the following second 3'-mRNA, ranging about 1~500 nucleotides apart in length.

3. The production method as defined in claim 2, wherein said multiple hairpin structures in the stem-loop RNA structure further contains a spacer sequence in between every two hairpin structures, ranging about 2~500 nucleotides apart in length.

4. The production method as defined in claim 1, wherein said second 3'-mRNA not only encodes at least one desired protein or peptide but also contains either SEQ.ID.NO.1 or SEQ.ID.NO.2 in its 3'-end.

5. The production method as defined in claim 1, wherein the stem-loop RNA structure further functions as an artificial internal ribosome entry site (IRES) mimic for initiating and enhancing translation of the second 3'-mRNA.

6. The production method as defined in claim 1, wherein after transfection into target cells, said mhmRNA construct are capable of being further translated into at least a desired protein/peptide for eliciting a pre-designed, desired biological effect or cellular function.

7. The production method as defined in claim 1, wherein said stem-loop RNA structure of said mhmRNA construct contain at least a sequence capable of being further processed in transfected cells after transfection to generate at least a shRNA and/or piRNA useful for silencing at least a specific target gene.

8. The production method as defined in claim 7, wherein said specific target genes include a variety of disease-associated cellular and viral genes.

9. The production method as defined in claim 1, wherein at least an additional helicase enzyme is added to the IVT reaction condition in order to facilitate the unwinding of RNA/DNA secondary structures.

10. The production method as defined in claim 1, wherein, said mhmRNA construct encodes at least an ingredient of an anti-viral vaccine.

11. The production method as defined in claim 1, wherein, said mhmRNA construct encodes at least an ingredient of an anti-cancer medicine.

12. The production method as defined in claim 1, wherein, said mhmRNA construct is further mixed with at least a delivery agent for cellular transfection in vitro, ex vivo or in vivo.

13. The production method as defined in claim 12, wherein said delivery agent includes glycylglycerins, liposomes, nanoparticles, liposomal nanoparticles, conjugating molecules, infusion chemicals, gene gun materials, electroporation particles, transposon, and a combination thereof.

14. The production method as defined in claim 1, wherein said preset buffer system contains 1× transcription buffer with additional 0.001~10 mM of betaine (trimethylglycine, TMG), dimethylsulfoxide (DMSO), or 3-(N-morpholino) propane sulfonic acid (MOPS), or a combination thereof.

15. The production method as defined in claim 1, wherein said mhmRNA construct further contains at least a modified nucleotide.

* * * * *